(12) United States Patent
Itskovitz-Eldor et al.

(10) Patent No.: US 7,247,477 B2
(45) Date of Patent: *Jul. 24, 2007

(54) METHODS FOR THE IN-VITRO IDENTIFICATION, ISOLATION AND DIFFERENTIATION OF VASCULOGENIC PROGENITOR CELLS

(75) Inventors: Joseph Itskovitz-Eldor, Haifa (IL); Sharon Gerecht-Nir, Haifa (IL)

(73) Assignee: Technion Research & Development Foundation Ltd., Haifa (IL)

( * ) Notice: Subject to any disclaimer, the term of this patent is extended or adjusted under 35 U.S.C. 154(b) by 506 days.

This patent is subject to a terminal disclaimer.

(21) Appl. No.: 10/211,522

(22) Filed: Aug. 5, 2002

(65) Prior Publication Data

US 2003/0194802 A1    Oct. 16, 2003

Related U.S. Application Data

(60) Provisional application No. 60/372,429, filed on Apr. 16, 2002.

(51) Int. Cl.
*C12N 5/00* (2006.01)
*C12N 5/08* (2006.01)

(52) U.S. Cl. ..................... 435/366; 435/325

(58) Field of Classification Search ............ 435/366, 435/325; 425/366
See application file for complete search history.

(56) References Cited

U.S. PATENT DOCUMENTS

2001/0041936 A1    11/2001    Corbitt et al.

2002/0045258 A1    4/2002    Bickenbach et al.

FOREIGN PATENT DOCUMENTS

WO    WO 00/70021    11/2000
WO    WO 01/81549    1/2001

OTHER PUBLICATIONS

Conley et al., The International Journal of Biochemistry and Cell Biology, 36:555-567, 2004.*
Odorico et al, Stem Cells, 19:193-204, 2001.*
Thomas et al, Methods: A Companion to Methods in Enzymology, 17:202-218, 1999.*
Yancopoulos et al, "Vascular-Specific Growth Factors and Blood Vessel Formation", *Nature*, 407:242-248, 2000.
Gittneberger-de Groot et al, "Smooth Muscle Cell Origin and Its Relation to Heterogeneity in Development and Disease", *Arterioscler Thromb. Vasc. Biol.*, 19:1589—1594, 1999.
Condorelli et al, "Cardiomyocytes Induce Endothelial Cells to Transdifferentiate Into Cardiac Muscle: Implications for Myocardium Regeneration", *PNAS*, 98(19):10733-10738, 2001.
Lammert et al, "Induction of Pancreatic Differentiation by Signals from Blood Vessels", *Science*, 294:564-567, 2001.

(Continued)

*Primary Examiner*—Michael C. Wilson

(57) ABSTRACT

There is provided a simplified and inexpensive method for the in-vitro identification, isolation and culture of human vasculogenic progenitor cells. The method and the progenitor cells isolated thereby can be used for in-vitro vascular engineering, treatment of congenital and acquired vascular and hematological abnormalities, for evaluation and development of drugs affecting vasculo- and angiogenic processes, and for further investigation into tissue differentiation and development.

3 Claims, 7 Drawing Sheets
(7 of 7 Drawing Sheet(s) Filed in Color)

OTHER PUBLICATIONS

Schuldiner et al, "Efects of Eight Growth Factors on the Differentiation of Cells Derived from Human Embryonic Stem Cells", *PNAS*, 97(21):11307-11312, 2000.

Nishikawa et al, "Progressive Lineage Analysis by Cell Sorting and Culture Identifies FLK1+ VE-Cadherin+Cells at a Diverging Point of Endothelial and Hemopoietic Lineages", *Development*, 125:1747-1757, 1998.

Itskovitz-Eldor et al, "Differentation of Human Embryonic Stem Cells into Embroid Bodies Comprising the Three Embrionic Germ Layers", *Molecular Medicine*, 6(2):88-95, 2000.

Matsumoto et al, "Liver Organogenesis Promoted by Endothelial Cells Prior to Vascular Function", *Science*, 294:559-563, 2001.

Carmeliet, P., "Mechanisms of Arteriogenesis", *Nature Medicine*, 6(3):389-395, 2000.

Ogawa et al, Step-Wise Divergence of Primitive and Definitive Haematopoietic and Endothelial Cell Lineages During Embryonic Stem Cell Differentiation, *Genes Cells*6(12):1113-1127, 201 (abstract).

Yamashita et al, "FlK1-Positive Cells Derived From Embryonic Stem Cells Serve as Vascular Progenitors", *Nature*, 408:92-96, 2000.

Kaufman et al, "Hematopoietic Colony-Forming Cells Derived From Human Embryonic Stem Cells", PNAS, 98(19):10716-10721, 2001.

Levenberg et al, "Endothelial Cells Cells Derived From Human Embryonic Stem Cells", PNAS, 99(7):4391-4396, 2002.

Nishikawa, S., "A Complex Linkage in the Developmental Pathway of Endothelial and Hematopoietic Cells", *Curr Opin Cell Biol.* ,13(6):673-8, 2001.

Ogawa et al, "Expression of α4-Integrin Defines the Earliets Precursor of Hematopoietic Cell Lineage Diverged from Endothelial Cells", *Blood*, 93(4):1168-1177, 1999.

Faloon et al, "Basic Fibroblast Growth Factor Positively Regulates Hematopoietic Development", Development, 127: 1931-1941, esp. p. 1931-1933, 2000.

Pfeifer et al. "Transgenesis by Lentiviral Vectors: Lack of Gene Silencing in Mammalian Embryonic Stem Cells and Preimplantation Embryos", Proc. Natl. Acad. Sci. USA, 99(4): 2140-2145, 2002.

Magyar et al. "Mass Production of Embryoid Bodies in Microbeads", Ann. NY Acad. Sci., 944: 135-143, 2001.

Rovira et al. "Stable In Vivo Expression of Glucose-6-Phosphate Dehydrogenase (G6PD) and Rescue of G6PD Deficiency in Stem Cells by Gene Transfer", Blood, 96(13): 4111-4117, 2000.

Ishiwata et al. "New Approach for the Establishment of Mouse Early Embryon Stem Cells and Induction of Their Differentiation", Human Cell, 14(4): 283-291, 2001.

Guan et al. "Embryonic Stem Cells In Vitro—Prospects for Cell and Development Biology, Embryotoxicology and Cell Therapy", Altex, 16(3): 135-141, 1999.

Koch et al. "Tissue Engineering With Chondrocytes", Facial Plastic Surgery, 18(1): 59-68, 2002.

Risbud "Tissue Engineering: Implications in the Treatment of Organ An Tissue Defects", Biogerontology, 2(2): 117-125, 2001.

Lee "Tissue-Engineered Human Living Skin Substitutes: Development and Clinical Application", Yonsei Med. Journal, 41(6): 774-779, 2000.

Atala "Engineering Tissues and Organs", Current Opinion in Urology, 9(6): 517-526, 1999.

Mueller-Klieser "Three-Dimensional Cell Cultures: From Molecular Mechanism to Clinical Applications", American Journal of Physiology, 273(4 Pt. 1): C1109-C1123, 1997.

Maria-Engler et al. "Microencapsulation and Tissue Engineering as An Alternative Treatment of Diabetes", Brazilian Journal of Med. Biol. Research, 34(6): 691-697, 2001.

Kawamoto et al. "Therapeutic Potential of Ex Vivo Expanded Endothelial Progenitor Cells for Myocardial Ischemia", Circulation, 103(5): 634-637, 2001.

Bach et al. "VE-Cadherin Mediates Endothelial Cell Capillary Tube Formation in Fibrin and Collagen Gels", Experimental Cell Research, 238: 324-334, 1998.

Feraud et al. "Embryonic Stem Cell-Derived Embryoid Bodies Development in Collagen Gels Recapitulates Sprouting Angiogenesis", Laboratory Investigation, 81(12): 1669-1681, 2001.

Kehat et al. "Human Embryonic Stem Cells Can Differentiate Into Myocytes With Structural and Functional Properties of Cardiomyocytes", The Journal of Clinical Investigation, 108(3): 407-414, 2001.

Tamborini et al. "C-Kit and C-Kit Ligand (SCF) in Synovial Sarcoma (SS): An mRNA Expression Analysis in 23 Cases", British Journal of Cancer, 85(3): 405-411, 2001.

Yamamura et al. "Expression of the Smooth Muscle Calponin Gene in Human Osteosarcoma and Its Possible Association With Prognosis", International Journal of Cancer (Pred. Oncol.), 79: 245-250, 1998.

Syed et al. "Differential Expression of Angiopoietin-1 and Angiopoietin-2 in Colon Carcinoma", Cancer, 92: 1138-1143, 2001.

Hicklin et al. "Monoclonal Antibody Strategies to Block Angiogenesis", DDT, 6(10): 517, 2001.

Peichev et al. "Expression of VEGFR-2 and AC133 by Circulating Human CD34+ Cells Identifies A Population of Functional Endothelial Precursors", Blood, 95(3) 952-958, 2000.

Reyes et al. "Origin of Endothelial Progenitors in Human Postnatal Bone Marrow", Journal of Clinical Investigation, 109: 337-346, 2002.

Corada et al. "Monoclonal Antibodies Directed to Different Regions of Vascular Endothelial Cadherin Extracellular Domain Affect Adhesion and Clustering of the Protein and Modulate Endothelial Permeability", Blood, 97: 1679-1684, 2001.

??? "Assessing Human Stem Cell Safety", Chap.10:93-97, "Mouse Embryonic Stem Cells", Appendix B: B-1-B-11.

Lumelsky et al. "Differentiation of Embryonic Stem Cells to Insulin-Secreting Structures Similar to Pancreatic Islets", Science, 292(5520): 1389-1394, 2001.

Shamblott et al. "Human Embryonic Germ Cell Derivatives Express A Broad Range of Developmentally Distinct Markers and Proliferate Extensively In Vitro", Proc. Natl. Acad. Sci. USA, 98(1): 113-118, 2001.

Quarmby et al. "Irradiation Induces Upregulation of CD31 in Human Endothelial Cells", Artesiosclerosis, Thrombosis, and Vascular Biology, 19(3): 588-597, 1999.

Faloon et al. "Basic Fibroblast Growth Factor Positively Regulates Hematopoietic Development", Development, 127: 1931-1941, 2000. p. 1931-1933.

Nakayama et al. "Vascular Endothelial Growth Factor Synergistically Enhances Bone Morphogenetic Protein-4-Dependent Lymphohematopoietic Cell Generation From Embryonic Stem Cells In Vitro", Blood, 95: 2275-2283, 2000.

Nishikawa "Embryonic Stem Cells as A Source of Hematopoietic and Vascular Endothelial Cells In Vitro", Journal of Allergy and Clinical Immunology, 100: S1-2-S1-4, 1997.

Feraud et al. "Angiogenesis Is Recapitulated During Embryonic Stem Cell-Derived Embryoid Body Development Into Type 1 Collagen Gels", Journal of Submicroscopic Cytology and Pathology, 32(3): 401, 2000.

Conway et al. "Molecular Mechanism of Blood Vessel Growth", Cardiovascular Research, 49: 507-521, 2001.

Lebowski et al. "Serum-Free Culture of Hematopoietic Stem Cells: A Review", Stem Cells, 13(6): 607-612, 1995. Abstract.

* cited by examiner

Figures 2A-M
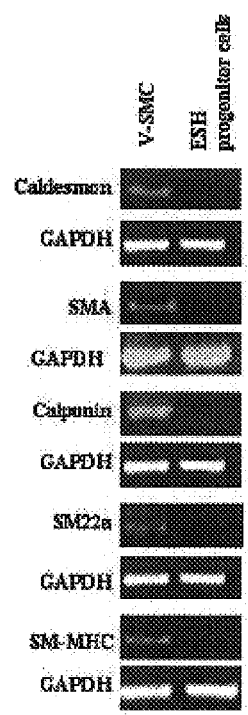
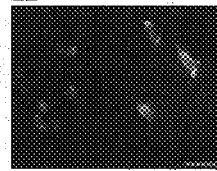 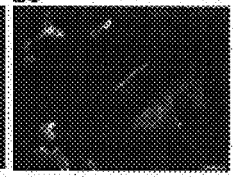 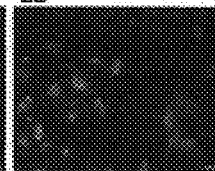 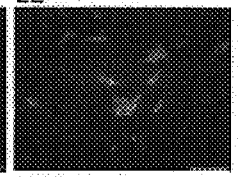
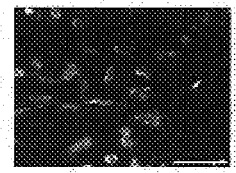 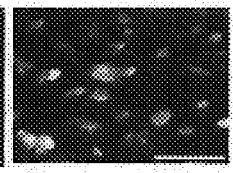 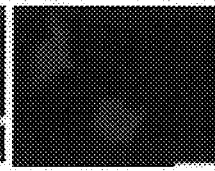 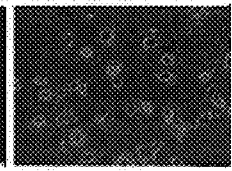
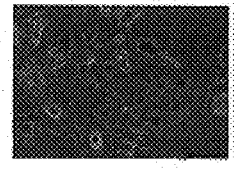 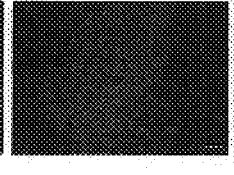 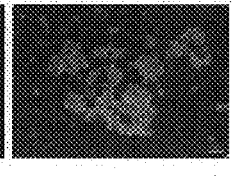 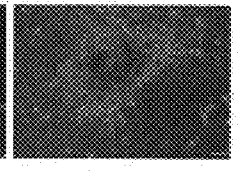

Fig. 4A
Fig. 4B
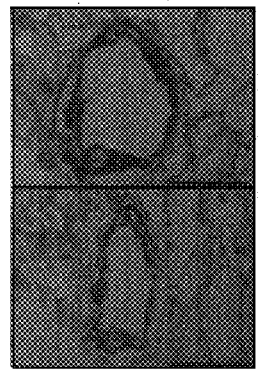
Fig. 5A
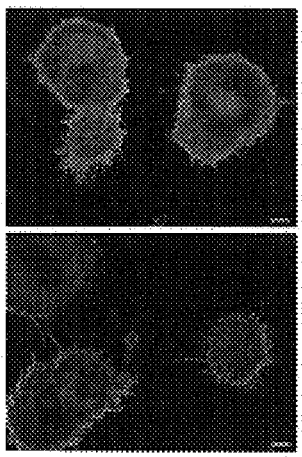
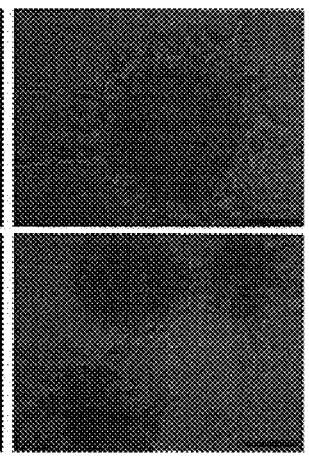
Fig. 5B
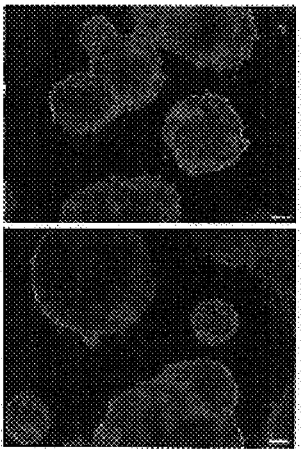
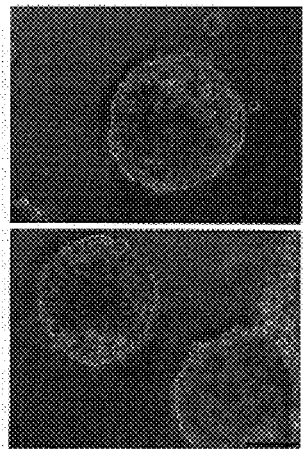

METHODS FOR THE IN-VITRO IDENTIFICATION, ISOLATION AND DIFFERENTIATION OF VASCULOGENIC PROGENITOR CELLS

This application claims the benefit of priority from U.S. Provisional Patent Application No. 60/372,429, filed Apr. 16, 2002.

FIELD AND BACKGROUND OF THE INVENTION

The present invention relates to novel methods for the isolation and culture of vasculogenic progenitor cells from stem cells and, more particularly, to methods for use of vasculogenic progenitor cells in tissue engineering, research and diagnostics.

Recently, techniques have been developed which allow human embryonic stem cells to proliferate indefinitely in culture, enabling experimentation with induction of differentiation in a directed, tissue-specific manner (Itskovitz-Eldor, J et al Mol Med 2000; 6:88–95, Reubinoff B E at al Nat Biotech 2000; 18:399–404, Schuldiner M et al PNAS USA 2000; 97:11307–12). Human embryonic stem cell growth and development is being carefully studied, and the rapidly accumulating knowledge is being employed in a variety of innovative therapeutic applications including in-vitro tissue engineering, transplantation medicine, generation of transgenic embryos and treatment of degenerative disease. Most significantly, the President of the U.S. has recognized the overwhelming importance of embryonic stem cells to medicine and research, and has recently sanctioned projects using existing human embryonic stem cell lines (White House Fact Sheet: Embryonic Stem Cell Research, Aug. 9, 2001). However, in-vitro manipulation of the complex steps of development, to reliably produce substantial amounts of desired cell lineages and specific phenotypes remains a crucially important goal.

Blood Vessel Formation in Embryonic Development and Adult Life

In the early stages of embryonic development, vessel formation occurs by a process referred to as vasculogenesis, in which mesodermally-derived endothelial cell progenitors undergo de-novo differentiation, expand and coalescence to form a network of primitive tubules (Yancopoulos G D et al Nature 2000; 407:242). These blood vessels are generally composed of two cell lineages, each serving a different function: internal endothelial cells that form the channels for blood conduction, but alone cannot complete vasculogenesis; and periendothelial smooth muscle cells that protect and stabilize the fragile channels from rupture and provide haemostatic control (Carmeliet P Nature Med 2000; 6:389). A third cell lineage, the hematopoietic cells, share a common progenitor with the vascular cells, and differentiate into the blood cells. In the vertebrate embryo vasculogenesis occurs in the paraxial and lateral mesoderm, giving rise to the primordia of the heart, the dorsal aorta, and large vessels of the head, lung and gastrointestinal system. Angiogenesis involves the maturation and remodeling of the primitive vascular plexus into a complex network of large and small vessels. Angiogenesis also leads to vascularization of initially avascular organs such as kidney, brain and limb buds.

Angiogenesis is also required postnatally for normal tissue growth, and continues throughout adult life, for example during neo-vascularization of the endometrium during normal female estrus, during pregnancy in the placenta, and during wound healing (Risau, et al Nature 1997; 386:671–674).

In addition, a number of diseases and disorders have been associated with abnormal endothelial growth: endothelial hyperproliferation in atherosclerosis, neovascularization in tumor growth and metastasis, and deregulated angiogenesis in rheumatoid arthritis, retinopathies, hemangiomas and psoriasis (Folkman et al Nature Med. 1995; 1: 27–31; Hanahan and Folkman, Cell 1996; 86:353–64).

Embryonic Endothelial Cells In-Vitro

Research into the functions, origin and nature of embryonic endothelial cells (EEC) has revealed that EECs can promote liver organogenesis (Matsumoto K et al Science 2001; 294:559), induce pancreas differentiation (Lammert E et al 2001; 294:564) and trans-differentiate into cardiac muscle cells under specific conditions (Condorelli G et al 2001; 98:10733). While the nature of differentiation and development of endothelial precursors is not yet fully understood, it is becoming clear that hematopoietic development and the generation of vascular smooth muscle cells (v-SMC) are tightly linked with vascular development.

Embryonic stem cells are difficult to maintain in culture, tending to spontaneously differentiate. For ongoing cultures, cells from the inner mass of blastocysts are typically grown on a layer of mouse embryonic fibroblast "feeder" cells to preserve their undifferentiated phenotype and proliferabilty (Keller, G M Curr Opin Cell Biol 1995; 7:862–69). In mice, early differentiation into embryonically distinct cell types can be induced by coculture with stromal cell lines (Palacios R, et al PNAS USA 1995; 92:7530–34), culture on substrates such as fibronectin, laminin, collagen, etc. (Ogawa M et al Blood 1999; 93: 1168–77) or in vitro aggregation of embryoid stem (ES) cells into "embryoid bodies" (EB), demonstrating regional differentiation into three germ layers (Keller, GM Curr Opin Cell Biol 1995; 7:862–69).

Murine Embryonic Stem Cells

Study of vasculogenic events in murine ES cells has been instructive. Both hematopoietic and endothelial cells have been observed in blast cell colonies generated from mouse ES cell-derived embryoid bodies (Choi K, et al Development 1998; 125:725). Also working with murine ES cells, Nishikawa and colleagues demonstrated that 3-D embryoid body formation was not required for differentiation of lateral mesoderm cells. When cultured non-aggregated mouse embryonic cells were grown on a collagen substrate, cells expressing vascular endothelial Cadherin (VE-cad+) were found to give rise to hematopoietic cells (Nishikawa S I, et al Development 1998; 125:1747, Nishikawa S I et al Immunity 1998; 8:761, and Fujimoto T, et al Genes Cells 2001; 6:1113). Where markers of smooth muscle cell (SMC) phenotype (e.g. surface markers and morphology) are observed, early periendothelial SMCs associated with embryonic endothelial tubes can be shown to trans-differentiate from the endothelium (Gittenberger de-Groot, A C et al, Atheroscler Thromb Vasc Biol 1999; 19:1589), and differentiation of embryonic common vascular progenitors (Flk1+) into endothelial and smooth muscle cells can been observed (Yamashita J et al Nature 2000; 408:92). However, attempts to directly extrapolate from mouse to human EC systems have met with disappointing results, indicating that many developmental processes and requirements are species specific (see, for example, Reubinoff B E et al, Nat. Biotechnolog. 2000; 18:399–404). Specifically, in contrast to it's expression in mouse embryonic stem (mES) cells, the vascular specific growth factor receptor VEGFR 2 (Flk-1/KDR) is expressed in undifferentiated hES cells (Kaufman, DS et al PNAS USA 2001; 98:10716–21) and does not increase during the first week of differentiation (Levenberg, S et al PNAS USA 2002; 99:4391–96), indicating that the timing of VEGFR 2 expression may vary among vertebrate species (also reviewed by Nishikawa; Nishikawa S I et al Curr Opin Cell Biol 2001; 13:862–69). Levenberg et al (Levenberg, S et al PNAS USA 2002; 99:4391–96) further reported that other endothelial markers, namely vascular endothelial cadherin (VE-cad) and platelet-endothelial cell adhesion molecule-1 (PECAM1/CD31), increased during the first week of hES differentiation. Clearly, coordination of expression of specific endothelial-specific factors, in the appropriate combinations, are crucial to human vasculogenesis.

Human Embryonic Stem Cells

Human embryonic stem (hES) cell lines were first derived in 1998 (Thomson, J A et al Science 1998; 282:1145; U.S. Pat. No. 6,200,806 to Thomson et al; U.S. Pat. No. 6,331,406 to Gearhart J D and Shamblott M J), and have recently been induced to differentiate in vitro in a cell lineage-specific manner (Schuldiner M et al PNAS 2000; 97:11307–312, International Patent Application WO0210347 A2 to Benvenisty, N). Since hES cells maintain the embryonic stem cell phenotype throughout hundreds of doubling times, and differentiate to all embryonic cell lineages, they provide a potentially unlimited source of cells for study and clinical application. Both hematopoietic and endothelial cell differentiation have been observed in human ES cells. To date, hematopoietic differentiation of the hES cells has required coculturing with either the S17 (murine bone marrow) or C166 (yolk sac endothelial) stromal cell lines, inducing the appearance of primary human hematopoietic tissue characteristics such as cell surface antigen CD34 and hematopoietic colony formation (Kaufman, D S et al PNAS USA 2001; 98:10716–21). In another recent study, endothelial cells were selected by cell sorting (FACS) from human embryoid bodies (EB) using monoclonal antibodies raised against the endothelial-specific marker PECAM-1 (Levenberg, S et al PNAS USA 2002; 99:4391–96). The selected, PECAM-1+ embryoid body-derived (EBD) cells exhibited endothelial-specific characteristics such as von Willebrand factor, VEGFR-2 and VE-cad surface markers and primitive, vessel-like cord formation when cultured on a soft substrate (Matrigel). PECAM-1+ EBD cells were further observed forming vascular structures in-vivo following seeding on biodegradable polymer matrix sponges and implantation into SCID mice. However, all of the abovementioned methods for differentiation of human ES require either coculturing with non-human cells or embryoid body formation prior to appearance of endothelial phenotypes, and immunofluorescent cell sorting for selection according to endothelial cell markers, rendering them both costly and unsuitable for many clinical applications. Thus, it would be advantageous to provide a simplified, less expensive method of culturing, selecting and directing differentiation of human embryonic stem cells, without the limitations of aggregation into embryoid bodies or immunofluorescent selection.

Prior art discloses a number of techniques and methods for preparation and use of embryonic stem cells for differentiation. Early techniques required inner-cell mass cells from blastocyst-stage embryos (fresh or cryopreserved) as a source of stem cells (see, for example, International Patent Application No. WO 0129206 A1 to Cibelli et al; U.S. Pat. Applications Nos. 20020045259 A1 to Lim et al, 20020004240 A1 to Wang). Many others rely upon aggregation of the stem cells into embryoid bodies for initiation of differentiation (see, for example, International Patent Application No. WO0070021 A3 to Itskovitz-Eldor J and Benvenisty N).

Various methods for differentiation of stem cells in culture have also been disclosed. International Patent Application No. WO 0134776 A1, U.S. Pat. Application No. 20020015694 A1, and U.S. Pat. No. 6,280,718, all to Kaufman, D et al, disclose methods of differentiating human embryonic stem cells into hematopoietic cells by coculture with mammalian stromal cells. U.S. Patent Application No. 20020023277 A1 to Stuhlmann, H et al discloses the identification and isolation of the vasculogenesis-related gene Vezf1 in mice, and methods for selection of endothelial cells and precursors based on Vezf1 expression. Also disclosed are methods for modulating angiogenesis, and diagnosis and treatment of vascular disease and neoplasm in a subject, the methods employing detection, measurement and modification of levels of Vezf1 in tissues. However, the transgenic ES cell experiments described were restricted to mouse embryoid body cells only, and neither human nor any other primate embryo cells were used. Furthermore, selection, according to the disclosure, is on the basis of Vezf1 expression, thus failing to overcome the abovementioned limitations of aggregation and immunofluorescent sorting.

U.S. Patent Application No. 20020039724 A1 to Carpenter, M K discloses methods for differentiation and selection of human embryonic neural progenitor cells, and therapeutic, diagnostic and investigative uses thereof. The disclosed human neural progenitor cells, for reconstitutive therapy of, for example, neural degenerative disease, are also derived from human embryoid bodies, and are selected and isolated according to expression and detection of neural cell specific markers, NCAM and A2B5. Similarly, International Patent Application WO 0181549 A3 to Rambhatla L and Carpenter MK discloses methods for treating embryoid bodies with n-butyrate for induction of differentiation into hepatocyte lineage cells. No mention is made of non-aggregated hES origins, or simplified methods of progenitor isolation in either application.

Recently, Benevenisty (International Patent Application WO 0210347 A2 to Benvenisty) disclosed methods for "directed differentiation" of human embryonic stem cells by treating aggregated, embryoid body-derived cells with exogenous factors, enriching the cultures for a specific lineage cell type. The factors used were known effectors of differentiation, such as retinoic acid, neuronal growth factor, epidermal growth factor, fibroblast growth factor, etc., and differentiation was determined by de novo gene expression, and the appearance of tissue lineage-specific cell surface markers.

U.S. Pat. Application No. 20010041668 A1, to Baron, M et al, discloses the use of extraembryonic, morphogenic gene products such as Hedgehog, TNF and WNT for modulation of hematopoiesis and vascular growth from mammalian adult and embryonic mesodermal-derived stem cells. Manipulation of the levels of these extra-embryonic gene products in the stem cell environment, via external application, or genetic engineering, for example, is disclosed for either enriching or diminishing the hematopoietic and/or vascular potential of stem cells for treatment and diagnosis of diseases involving blood abnormalities, hypervascularization, neovascularization and revascularization of tissues. However, although treatment of human embryonic tissues is proposed, no examples using human adult or embryonic cells are presented, and no methods for culture or selection of non-aggregated embryonic stem cells, designed to overcome the abovementioned limitations, are disclosed.

Thus, there exists a need for a simplified and inexpensive method for the in-vitro identification, isolation and culture of human vasculogenic progenitor cells. Such a method and the progenitor cells isolated thereby can be used for in-vitro vascular engineering, treatment of congenital and acquired vascular and hematological abnormalities, for evaluation and development of drugs affecting vasculo- and angiogenic processes, and for further investigation into tissue differentiation and development.

SUMMARY OF THE INVENTION

According to one aspect of the present invention there is provided a method of preparing vasculogenic progenitor cells from undifferentiated ES cells, the method effected by culturing individual undifferentiated ES cells in a manner suitable for inducing differentiation of the undifferentiated ES cells into vasculogenic progenitor cells, thereby obtaining a mixed population of cells; and isolating cells smaller than 50 µm from said mixed population of cells, said cells smaller than 50 µm being vasculogenic progenitor cells.

According to another aspect of the present invention there is provided a method of preparing epithelial progenitor cells from undifferentiated ES cells, the method effected by culturing individual undifferentiated ES cells in a manner suitable for inducing differentiation of the undifferentiated ES cells into vasculogenic progenitor cells thereby obtaining a mixed population of cells; and isolating cells larger than 50 µm from said mixed population of cells, said cells larger than 50 µm being epithelial progenitor cells.

According to yet another aspect of the present invention there is provided a method of preparing somatic cells from a population of vasculogenic progenitor cells, the method effected by obtaining a population of vasculogenic progenitor cells; and culturing the population of vasculogenic progenitor cells in the presence of at least one growth factor suitable for inducing somatic cell differentiation.

According to still another aspect of the present invention there is provided a method of preparing vascular tissue, the method effected by obtaining a population of vasculogenic progenitor cells; and culturing the population of vasculogenic progenitor cells in the presence of at least one vasculogenic and/or angiogenic growth factor, under conditions suitable for inducing vascular tissue differentiation.

According to further features in preferred embodiments of the invention described below the population of vasculogenic progenitor cells is cultured in a semi-solid, vascularization-promoting medium.

According to yet further features in preferred embodiments of the invention described below the population of vasculogenic progenitor is cultured on a 3-dimensional scaffold.

According to still further features in preferred embodiments of the invention described below the vasculogenic and/or angiogenic factor is selected from the group consisting of vascular endothelial growth factor (VEGF), angiopoietin (Ang), platelet derived growth factor (PDGF), ephrin (Eph), fibroblast growth factor (FGF), tumor growth factor (TGF) and placental growth factor (PlGF).

According to an additional aspect of the present invention there is provided a method of determining an effect of a factor on vascular development, growth and/or modification, the method effected by obtaining a population of vasculogenic progenitor cells; exposing the population of vasculogenic progenitor cells to the factor; and determining an effect of the factor on the population of vasculogenic progenitor cells to thereby determine the effect thereof on vascular development.

According to further features in preferred embodiments of the invention described below the factor is a substance and/or an environmental factor.

According to yet further features in preferred embodiments of the invention described below the factor is a putative angiogenesis and/or vasculogenesis downregulator, whereas the method further includes culturing the population of vasculogenic progenitor cells under conditions suitable for promoting angiogenesis and/or vasculogenesis.

According to still further features in preferred embodiments of the invention described below the factor is a putative angiogenesis and/or vasculogenesis upregulator, whereas the method further includes culturing the population of vasculogenic progenitor cells under conditions limiting angiogenesis and/or vasculogenesis.

According to a further aspect of the present invention there is provided a method of relieving or preventing a vascular disease or condition in a mammalian subject, the method effected by obtaining a population of vasculogenic progenitor cells; and administering the vasculogenic progenitor cells into the subject under conditions suitable for stimulating differentiation of the vasculogenic progenitor cells into endothelial and smooth muscle cells.

According to further features in preferred embodiments of the invention described below the vascular disease or condition is selected from a group consisting of congenital vascular disorders, acquired vascular disorders and ischemia/reperfusion injury.

According to yet a further aspect of the present invention there is provided a method of vascularizing a mammalian tissue, the method effected by obtaining a population of vasculogenic progenitor cells contacting the vasculogenic progenitor cells with the mammalian tissue under conditions suitable for stimulating differentiation of the vasculogenic progenitor cells into endothelial and smooth muscle cells.

According to further features in preferred embodiments of the invention described below the mammalian tissue is an engineered, non-vascular tissue in need of vascularization and/or an embryonic tissue.

According to further features in preferred embodiments of the invention described below contacting the vasculogenic progenitor cells with the mammalian tissue is performed in vitro or in vivo.

According to still a further aspect of the present invention there is provided a method of relieving or preventing a hematological disease or condition in a mammalian subject, the method effected by obtaining a population of vasculogenic progenitor cells; and administering the vasculogenic progenitor cells into the subject under conditions suitable for stimulating differentiation of the vasculogenic progenitor cells into endothelial and blood cells.

According to further features in preferred embodiments of the invention described below the hematological disease or condition is selected from a group consisting of congenital blood disorders, acquired blood disorders, clotting disorders and neoplastic disease.

According to further features in preferred embodiments of the invention described below obtaining the population of vasculogenic cells is effected by culturing individual undifferentiated ES cells in a manner suitable for inducing differentiation of the undifferentiated ES cells into vasculogenic progenitor cells thereby obtaining a mixed population of cells and isolating cells smaller than 50 µm from said mixed population of cells.

According to still an additional aspect of the present invention there is provided a composition of matter comprising a substrate and a population of vasculogenic progenitor cells, wherein said vasculogenic progenitor cells are prepared from undifferentiated ES cells by a method effected by the steps: culturing individual undifferentiated ES cells in a manner suitable for inducing differentiation of the undifferentiated ES cells into vasculogenic progenitor cells thereby obtaining a mixed population of cells and isolating cells smaller than 50 μm from said mixed population of cells, said cells smaller than 50 μm being vasculogenic progenitor cells.

According to further features in preferred embodiments of the invention described below the substrate is selected from the group consisting of matrigel, collagen gel, and polymeric scaffold.

According to still further features in preferred embodiments of the invention described below the vasculogenic progenitor cells is contacted with the substrate in a manner so as to induce vascular development within the substrate.

According to further features in preferred embodiments of the invention described below the hematological disease or condition is selected from a group consisting of congenital blood disorders, acquired blood disorders, clotting disorders and neoplastic disease.

According to yet further features in preferred embodiments of the invention described below culturing the individual undifferentiated ES cells is effected by subjecting the undifferentiated ES cells to at least one condition selected from a group consisting of avoiding aggregation of ES cells, growth on collagen, cell seeding concentration between $2 \times 10^4$ and $1 \times 10^5$ cells/cm$^2$ and presence of differentiation medium.

According to still further features in preferred embodiments of the invention described below the undifferentiated ES cells are human ES cells.

According to an additional aspect of the present invention there is provided a method of preparing endothelial cells from vascular tissue, the method effected by subjecting the vascular tissue to conditions designed for dissociating cells from the vascular tissue, thereby obtaining a mixed population of dissociated cells and isolating cells smaller than 50 μm from said mixed population of cells.

According to a further aspect of the present invention there is provided a method of preparing epithelial cells from vascular tissue, the method effected by subjecting the vascular tissue to conditions designed for dissociating cells from the vascular tissue, thereby obtaining a mixed population of dissociated cells, thereby obtaining a mixed population of individual cells; and isolating cells larger than 50 μm from said mixed population of cells.

According to further features in preferred embodiments of the invention described below the vascular tissue is human vascular tissue According to yet further features in preferred embodiments of the invention described below the cells smaller or larger than 50 μm are isolated via filtration, morphometry and/or densitometry.

According to still further features in preferred embodiments of the invention described below the filtration is effected via a filter having a pore size smaller than 50 μm.

According to yet an additional aspect of the present invention there is provided a cell culture comprising a population of vasculogenic progenitor cells being sustainable in a proliferative state for at least 14 days and being capable of differentiation into smooth muscle, endothelial and/or hematopoietic cells upon exposure to at least one growth factor selected from the group consisting of vascular endothelial growth factor (VEGF), angiopoietin (Ang), platelet derived growth factor (PDGF), ephrin (Eph), fibroblast growth factor (FGF), tumor growth factor (TGF), placental growth factor (PlGF), cytokines, erythropoietin, thrombopoietin, transferrin, insulin, stem cell factor (SCF), Granulocyte colony-stimulating factor (G-CSF) and Granulocyte-macrophage colony stimulating factor (GM-CSF).

According to further features in preferred embodiments of the invention described below the population of vasculogenic progenitor cells is capable of expressing at least one exogenous polypeptide selected from the group consisting of cell-surface markers, cell-surface antigens, angiogenic factors, vasculogenic factors and hematopoietic factors.

According to still further features in preferred embodiments of the invention described below the exogenous polypeptide is expressed in an inducible manner.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1A:
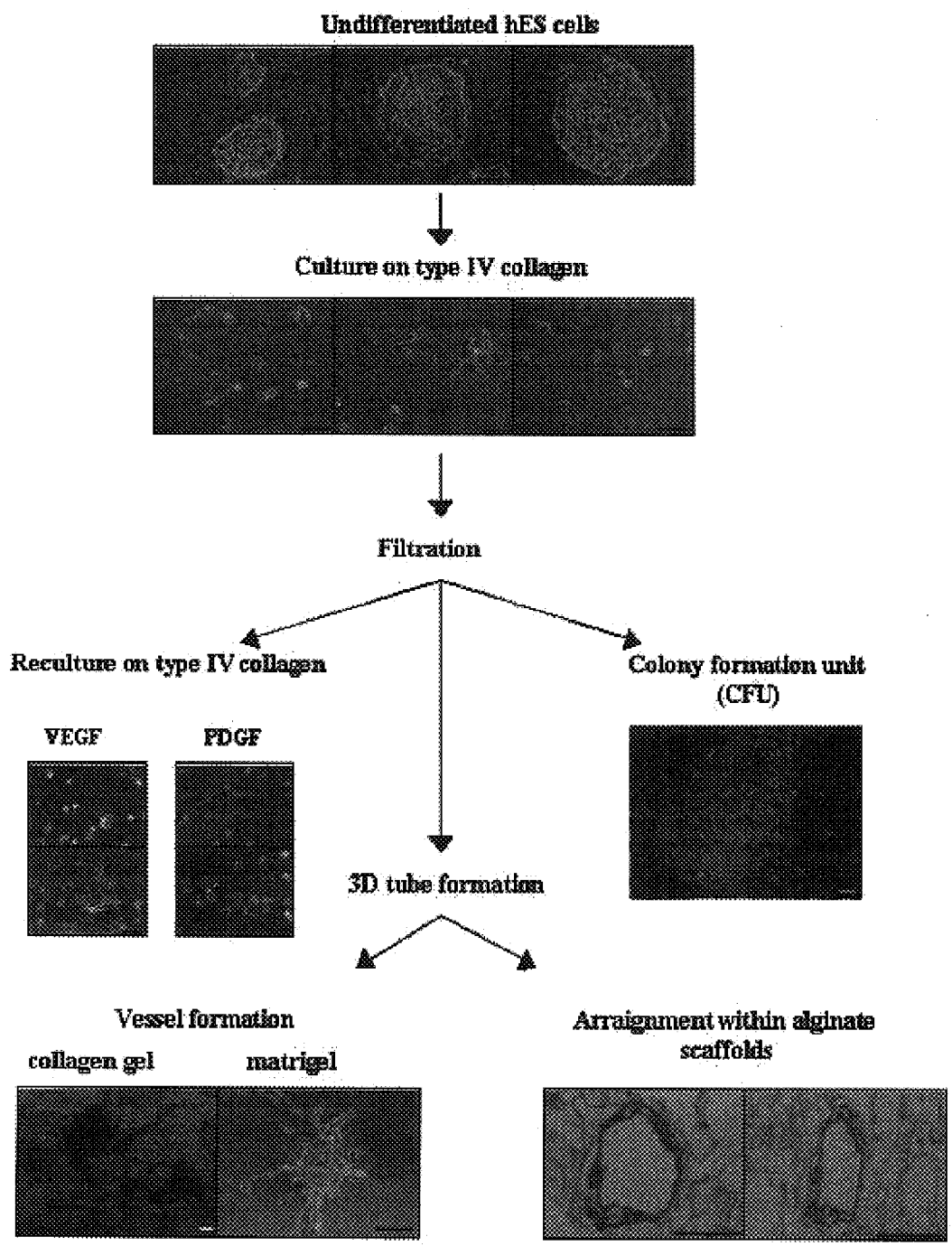
Figure 1B:
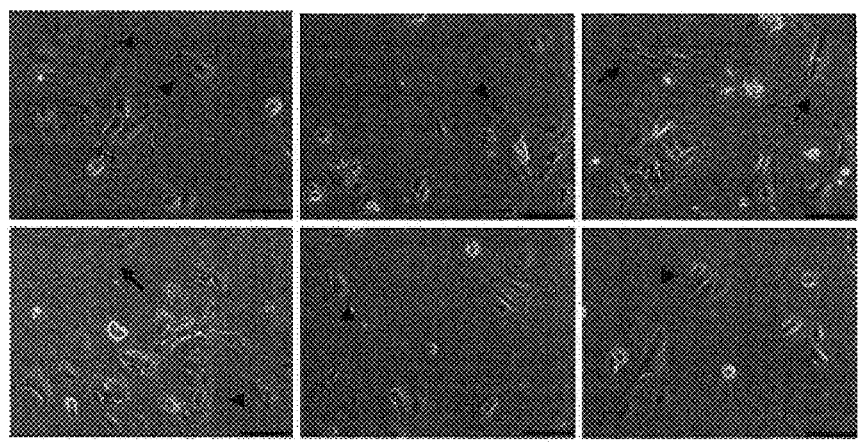
Figure 1C:
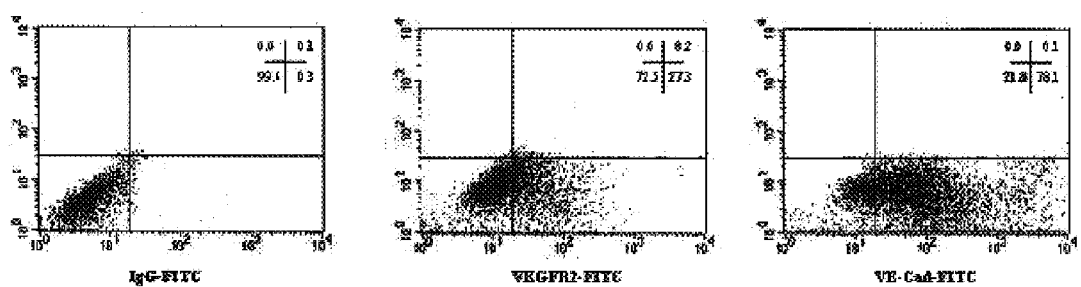
Figures 1D, 1E:
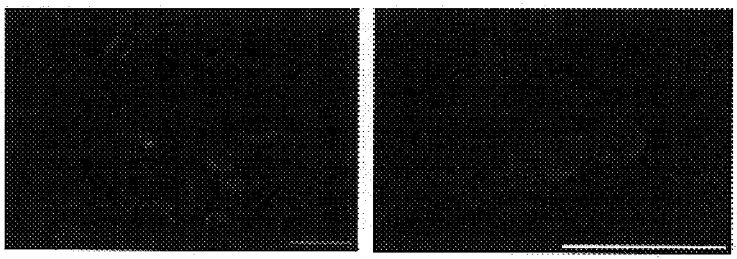
Figure 1F:
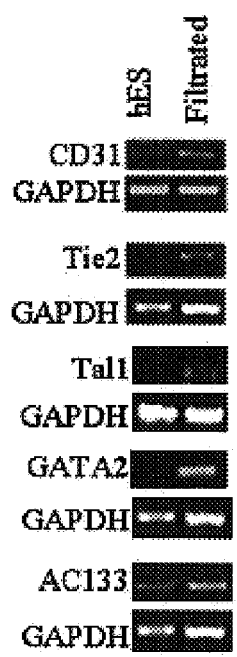
Figure 1G:
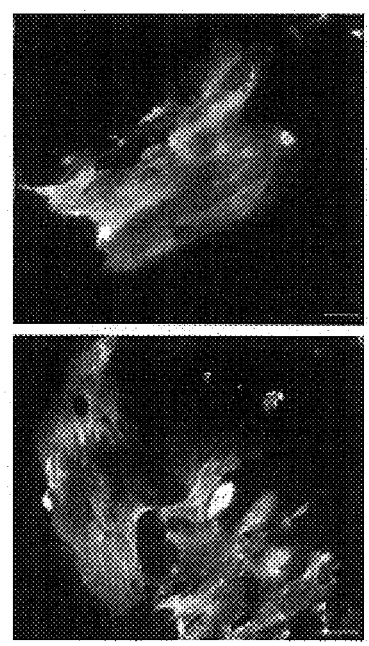
Figure 1H:
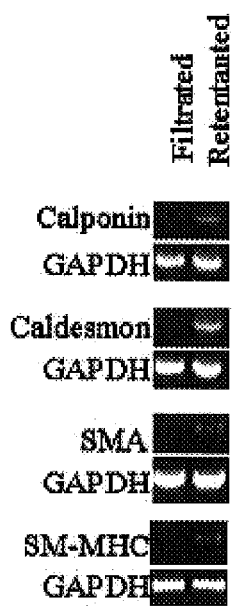
Figure 1I:
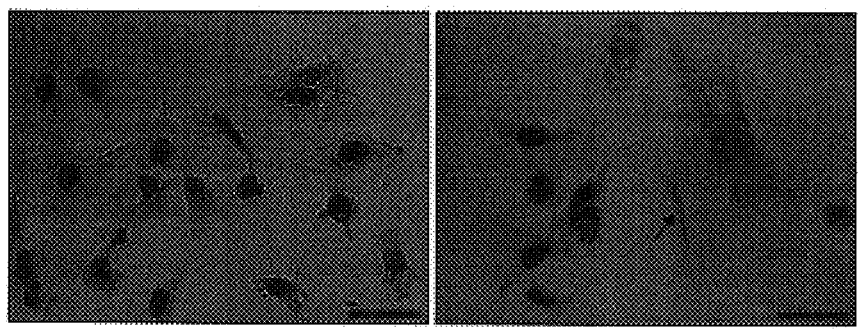

FIGS. 1A–H provide an outline for, and micrographs demonstrating the culture-based selection for human ES cell-derived vasculogenic progenitor cells. FIG. 1A illustrates the outline of the differentiation-selection procedure. FIG. 1B is a series of micrographs demonstrating the divergent morphology of the cells following 6 days culture on collagen: note the large, flat fiber-bearing cells (arrows) and the smaller, flattened cells with large nuclei (arrowheads). FIG. 1C is a series of graphs demonstrating a FACS analysis of endothelial cell surface markers in the filtered, isolated vasculogenic progenitors cells. Filtered cells were exposed to primary antibodies to VE-cadhedrin (VE-cad), VEGFR2 (VEGFR2), and to fluorescent labeled anti-IgG, or to the second antibody alone (IgG-FITC). Note the high proportion of cells (78%) expressing VE-cad. FIGS. 1D–E are photographs demonstrating the indirect immunomorphological analysis of VE-cad expression on filtered, isolated vasculogenic progenitors cells. Immunofluorescent staining of fixed and plated 12 hour cultures of the filtered cells demonstrate strong localization of VE-cad, at cell-cell adherent junctions, visible at higher magnification (FIG. 1E). FIG. 1F is a photograph of EtBr stained gels demonstrating the expression of endothelial and hematopoietic markers in the isolated vasculogenic progenitors cells. Expression of the CD31 and Tie2 endothelial markers and the Tal1, GATA2 and AC 133 early vasculogenic progenitor markers was compared in total RNA from the smaller, flat filtered cells (Filtrated), and the undifferentiated human embryonic stem (hES) cells by RT-PCR. The housekeeping marker GAPDH serves as an internal standard of amplification. Note the prominent, endothelial, smooth muscle and hematopoietic (ESH)-specific expression of the CD31, Tie2, Tal1 and GATA2 markers. FIG. 1G is a fluorescent micrograph of the larger, flat cells retained by filtration, demonstrating the presence of the epitheliod phenotype smooth muscle cell marker α-sma not detected in the smaller, human vasculogenic progenitor cells. FIG. 1H is a photograph of EtBr stained gels demonstrating the expression of epitheliod markers in the isolated, larger retained cells. Expression of the Calponin, Caldesmon, smooth muscle actin (SMA) and SM-MHC markers was compared in total RNA from the larger, flat retained cells (Retained), and the smaller, human vasculogenic progenitor (Filtrated) cells by RT-PCR. The housekeeping marker GAPDH serves as an internal standard of amplification. Note the absence of expression of all of the smooth muscle cell markers in the human vasculogenic progenitor cells, and their prominent expression in the Retained cells. FIG. 1I is a micrograph of BrdU incorporation in both smaller, filtered (left panel), and larger, retained cells (right panel), demonstrating active proliferation of the smaller, human vasculogenic progenitor cells. Note the active uptake of BrdU in the smaller, darkened cell nuclei, contrasted with the minimal incorporation in the larger, non-proliferating retained cells (arrow). Bar equals 10 µm.

FIGS. 2A–M are microscopic, immunofluorescence and RT-PCR studies of cultured common human vasculogenic progenitor cells, demonstrating specific growth factor-mediated induction of endothelial or smooth muscle cell characteristics. FIG. 2A is a photograph of EtBr stained gels demonstrating the expression of smooth muscle cell markers in common human vasculogenic progenitor cells recultured on type IV collagen at $2.5 \times 10^4$ cells/cm$^2$ for 10–12 days with 10 ng/ml hPDGF-BB (R and D Systems, Inc., Minneapolis, Minn., USA). Expression of the smooth muscle cell markers Caldesmon, smooth muscle actin (SMA), Calponin, SM22α and SM-MHC markers was compared in total RNA from the growth factor-treated cells (v-SMC), and the untreated human vasculogenic progenitor (ESH progenitor) cells by RT-PCR. The housekeeping marker GAPDH serves as an internal standard of amplification. Note the absence of expression of all of the smooth muscle cell markers in the ESH cells, and their prominent expression in the hPDGF-BB treated cells. FIGS. 2B–E are photomicrographs of immunofluorescent detection of smooth muscle cell markers expressed in the human platelet-derived growth factor (hPDGF)-BB-treated human vasculogenic progenitor cells. Fixed preparations of treated cells were stained with primary antibodies to: α SMA (FIG. 2B); smoothelin (FIG. 2C); SM-MHC (FIG. 2D), and Calponin (FIG. 2E), immunodetected with fluorescent second antibodies and visualized via fluorescent microscopy. Note the staining of both epitheliod and spindle-shaped cell types in the growth factor-treated cultures. FIGS. 2F–H are photomicrographs showing the detection of endothelial cell markers expressed in human vasculogenic progenitor cells recultured on type IV collagen at $2.5 \times 10^4$ cells/cm$^2$ for 10–12 days with 50 ng/ml h VEGF$_{165}$ (R and D Systems, Inc. Minneapolis, Minn., USA). Growth factor-treated cells were fixed and immunedetected as described hereinabove with anti-VEcad (FIG. 2F), or anti-von Willebrand Factor (vWF)(FIG. 2G) antibodies. Note the localization of anti vWF staining in the Weibel-Palade bodies (FIG. 2G). Uptake of DiIl-labeled ac-LDL (10 µg/ml, 4 hours, 37° C.)(FIG. 2$h$) was also detected (FIG. 2H). FIGS. 2I and 2J are micrographs of BrdU incorporation in both platelet derived (PDGF) (FIG. 2J) and vascular endothelium (VEGF) (FIG. 2I) growth factor-treated human vasculogenic progenitor cells, demonstrating active proliferation (staining) of the endothelial-type cells. Note the appearance of stress fibers (FIG. 2I, arrow), and the active uptake of BrdU in the darkened cell nuclei of the VEGF-treated cells (FIG. 2I), contrasted with the reduced incorporation of the larger hPDGF-BB treated cells (FIG. 2J). FIGS. 2K–2M are micrographs of hematopoietic colonies formed from human vasculogenic progenitor cells. ESH cells were selected, and cultured in a semisolid medium supplemented with cytokines to promote hematopoietic differentiation. Note the characteristic appearance of hematopoietic colonies (CFU) detected after 12 days incubation.

Figure 3A:
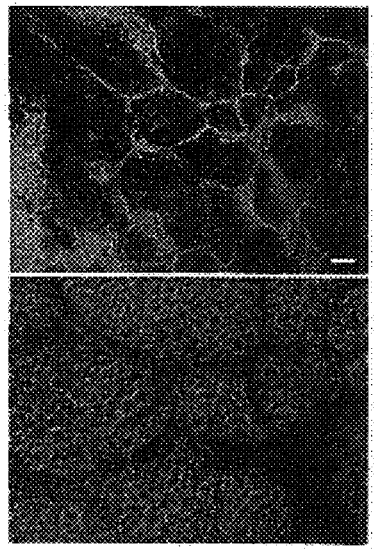
Figure 3B:
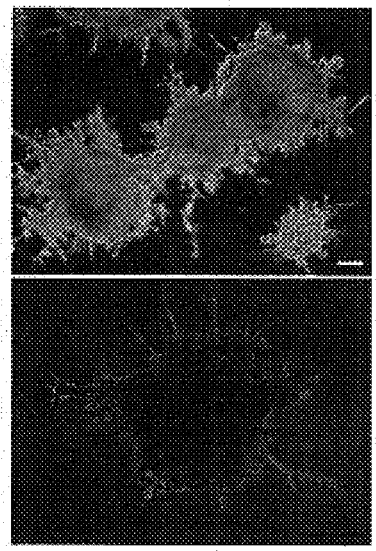
Figure 3C:
Figure 3D:
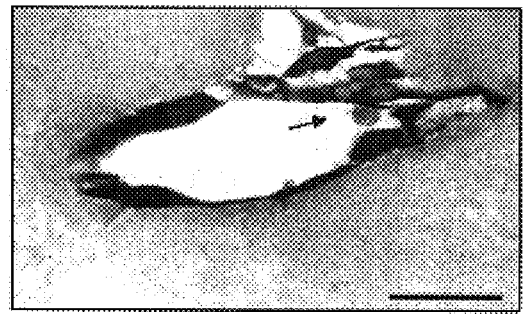
Figure 3E:
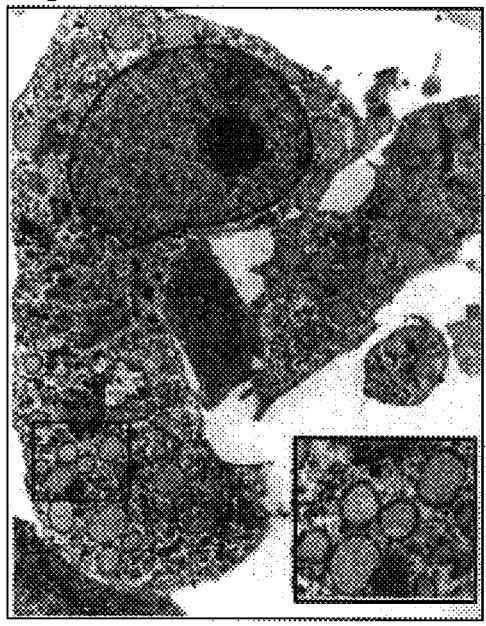
Figure 3F:
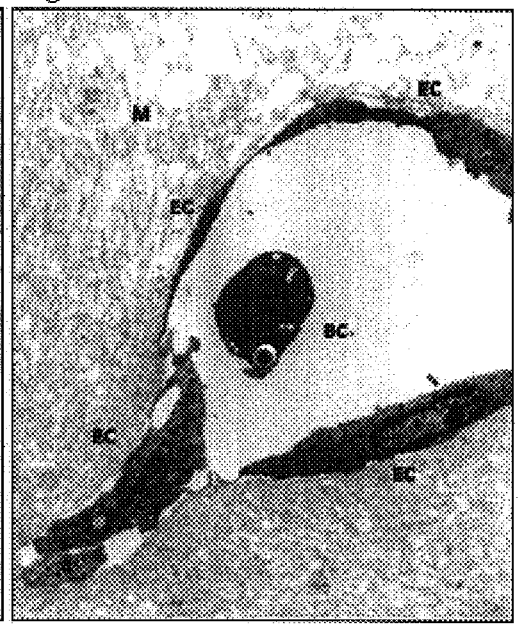
Figure 3G:
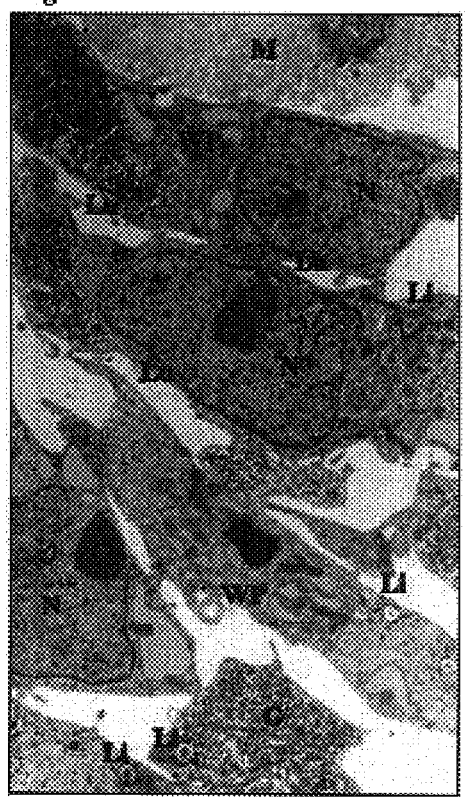

FIGS. 3A–G are photomicrographs (FIGS. 3A–D), and electron micrographs (FIGS. 3E–G) showing vascular structure formation in growth-factor-treated human vasculogenic progenitor (ESH) cells. Aggregated (24 hours in differentiation medium supplemented with 50 ng/ml hVEGF$_{165}$ and 10 ng/ml hPDGF-BB) ESH cells seeded onto type I collagen (FIG. 3A) or in matrigel (FIG. 3B) demonstrated vascular formation after 7 days growth (Note sprouting and tubular structures in both histology sections). Toluidine blue-stained sections of the same preparation revealed endothelial cell penetration and formation of a vascular-network structure in the matrigel (FIG. 3C) and, with higher magnification, a white blood cell formed within a vessel (arrow, FIG. 3D). Bar equals 10 µm (FIGS. 3A–C) or 20 µm (FIG. 3D). FIGS. 3E–G are electron micrographs of vessel formation in Matrigel, showing well-formed Weibel-Palade bodies (FIG. 3E, ×6,000 magnification, inset, ×12,000), typical of endothelial cells. FIG. 3F clearly demonstrates the presence of a darkly staining (due to Hemoglobin) blood cell (BC) in the center of a vessel formed by elongated endothelial cells (EC) within the matrigel (M) (×5,000 magnification). FIG. 3G demonstrates typical arrangement of endothelial cells (N-nucleus) within the matrigel (M), containing a clearly discernible lumen (Lu), characteristic lipoprotein capsules (Li), Weibel-Palade bodies (WP) and glycogen (G) (FIG. 3G, ×5,000 magnification).

FIGS. 4A–B are photomicrographs of histology sections depicting the in vitro vascularization of 3-D alginate scaffolds by human vasculogenic progenitor (ESH) cells. ESH aggregates were seeded on 1f120 50 µl alginate scaffolds in vitro in differentiation medium supplemented with 50 ng/ml hVEGF$_{165}$ and 10 ng/ml hPDGF-BB, and incubated for 14 days. FIG. 4A shows vessel formation around two representative scaffold pores. Higher magnification (FIG. 4B) reveals typical vascular wall structure of elongated flat endothelial cells with an adjacent layer of smooth muscle cells. Bar equals 10 µm.

FIGS. 5A–B are two series of photomicrographs demonstrating the sensitivity of ESH-derived vascular tissue to inhibitors of angiogenesis. ESH aggregates were seeded on matrigel and incubated for 7 days in differentiation medium supplemented with 50 ng/ml hVEGF$_{165}$ and 10 ng/ml hPDGF-BB alone (FIG. 5A) or with the addition of 50 µg/ml angiogenesis inhibiting anti VE-cad monoclonal antibody (clone BV6, CHEMICON INTNL, Inc. Temecula Calif., USA)(FIG. 5B). Note the lack of cellular projections and absence of tube and network structures in the anti VE-cad treated cultures (FIG. 5B). Bar equals 10 µm.

DESCRIPTION OF THE PREFERRED EMBODIMENTS

The present invention is of novel methods which can be used for simple and inexpensive preparation of vasculogenic progenitor cells, and cell cultures and compositions thereof prepared from, for example, human stem cells. Specifically, the present invention can be used for isolating vasculogenic progenitor cells from stem cells, and for in vitro growth and differentiation of the isolated vasculogenic progenitor cells for use in, for example, tissue engineering, angiogenesis research, therapeutic and diagnostic applications.

The principles and operation of the present invention may be better understood with reference to the drawings and accompanying descriptions. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Recent research studies have illustrated that embryonic cells can potentially serves as a source for pluripotent cells. Such cells are useful in human therapy since they posses the capacity to differentiate into a plurality of cell types (R. A. Pedersen, Scientif. Am. 1999; 280:68). Early work on embryonic stem cells was done using inbred mouse strains as a model. Compared with mouse ES cells, monkey and human pluripotent cells have proven to be much more fragile, and do not respond to the same culture conditions and manipulations.

Recently, human embryonic stem cells (hES) and germ-line (hEG) cells have been isolated and maintained in culture. Both human embryonic hES and hEG cells have the long-sought characteristics of human pluripotent stem cells, they are capable of ongoing proliferation in vitro without differentiating, they retain a normal karyotype, and they retain the capacity to differentiate to produce all adult cell types. However, spontaneous somatic differentiation of hES and hEG cells in culture proceeds without any consistent pattern of structural organization, generating multicellular aggregates of cell populations with a highly heterogeneous mixture of phenotypes, representing a spectrum of different cell lineages (Reubinoff, B E, et al Nat Biotech 2001; 19:1134).

Prior art studies describe various methods suitable for isolation of progenitor cells of specific cell type lineages from ES cells, however, such methods are typically extremely complex and costly. Initially, human embryonic stem cells are either grown on a mammalian stromal cell layer (see, for example, U.S. Pat. No. 6,280,718 to Kaufman, D S and Thomson, J A), in a live host as a teratoma (Thomson J A et al Science 1998; 282:1145–47) or aggregated in suspension into a multicellular structure known as the embryoid body (EB) (see, for example, International Pat. Application No. WO0070021 A3 to Itskovitz-Eldor J and Benvenisty N; and International Pat. Application WO0210347 A2 to Benvenisty N), and exposed to differentiation factors, typically producing a mixed population of cell types and lineages. Isolation of progenitor cells of specific lineages is then accomplished on the basis of immunodetection of lineage-specific markers, and separation of cell lineages by fluorescent or magnetic sorting (see, for example, International Pat. Application No. WO0181549 A3 to Rambhatla L and Carpenter, M K; U.S. Pat. No. 6,280,718 to Kaufman, D S and Thomson, J A; International Pat. Application No. WO0129206 A1 to Cibelli, J et al; and International Pat. Application No. WO 0168815 A1 to Pera, M F and Ben-Hur T). All of the abovementioned methods suffer from similar disadvantages: initial ES differentiation into progenitor cells involves many complex manipulations and interactions with the stromal cell layer, live host tissues or other EB cells. Furthermore, selection according to expression or display of cell surface markers is inefficient, requiring even more extensive manipulation, incurring great expense for reagents and detection equipment, and endangering the vitality and sterility of the progenitor cells.

While reducing the present invention to practice the present inventors have uncovered that vasculogenic progenitor cells may be prepared simply and inexpensively from embryonic stem cells by preventing aggregation, culturing on type IV collagen with specific endothelial differentiation factors and employing simple and efficient size selection methods. The vasculogenic progenitor cells prepared by the present invention are advantageous in that they can be further expanded in culture, can be induced to differentiate into endothelial, mural and hematopoietic tissue in vitro, form both small and large vascular structures when seeded on appropriate substrate, may be genetically manipulated and are suitable for tissue engineering, diagnostic and research purposes.

Thus, according to one aspect of the present invention there is provided a method of preparing vasculogenic progenitor cells from undifferentiated ES cells, such as human ES cells. The method, according to this aspect of the present invention, is effected by culturing individual undifferentiated ES cells in a manner suitable for inducing differentiation of the undifferentiated ES cells into vasculogenic progenitor cells, thereby obtaining a mixed population of cells, and isolating cells smaller than 50 µm from the mixed population of cells. Cell isolated in this manner are vasculogenic progenitor cells as is clearly illustrated in the Examples section hereinunder.

As used herein, the phrase "vasculogenic progenitor cells" refers to a population of cells that can generate progeny that are endothelial or smooth muscle precursors (such as angioblasts) or mature endothelial or smooth muscle cells, or hematopoietic precursor (such as erythroid colony forming units and megakaryocytes) or mature blood cells (such as erythrocytes and leukocytes). Typically, vasculogenic progenitor cells express some of the phenotypic markers that are characteristic of the endothelial, smooth muscle and hematopoietic lineages. Typically, they do not produce progeny of other embryonic germ layers when cultured by themselves in vitro, unless dedifferentiated or reprogrammed. It will be appreciated that it is not implied that each of the cells within the population have the capacity of forming more than one type of progeny, although individual cells that are multipotent vasculogenic progenitor cells may be present.

As used herein the, the terms "totipotent", "pluripotent" and "multipotent" refer to cells having decreasing degrees of developmental plasticity. Totipotent cells are capable of developing into all cell types or complete organisms (e.g.

blastomeres), pluripotent cells capable of differentiating into all cell types (e.g. ES cells) and multipotent cells are capable of differentiating into cells of specific lineages only (e.g. vasculogenic progenitor cells).

As used herein, the term "endothelial progenitor cell" or "endothelial precursor cell" refers to a cell that can generate mature endothelial cells. These cells may or may not have the capacity to generate hematopoietic or smooth muscle cells.

As used herein, the term "epithelial progenitor cell" or "epithelial precursor cell" refers to a cell that can generate mature smooth muscle cells.

As used herein, the term "hematopoietic progenitor cell" or "hematopoietic precursor cell" refers to a cell that can generate mature blood cells.

Embryonic stem cells are described as "undifferentiated" when a substantial portion of stem cells and their derivatives in the population display morphological characteristics of undifferentiated cells, clearly distinguishing them from differentiated cells of embryonic or adult origin. Undifferentiated ES cells are easily recognized by those skilled in the art, and typically appear in a microscopic view as cells with high nuclear/cytoplasm ratios and prominent nucleoli. Similarly, undifferentiated cells can be distinguished from differentiated cells by the absence of lineage specific markers such as vascular endothelial growth factor receptor 2 (VEGFR2), vascular endothelial cadherin (VE-cad) or platelet-endothelial cell adhesion molecule-1 (PECAM-1).

As used herein, the term "differentiated cell" refers to a cell that has progressed down a developmental pathway. Thus, pluripotent embryonic stem cells can differentiate to lineage-restricted precursor cells, such as neural progenitor, hepatocyte progenitor or hematopoietic cells, which are pluripotent for neural cells, hepatocytes and blood cell types, respectively; and the endothelial, smooth muscle and blood cell types listed above. These in turn may be differentiated further into other types of precursors further down the pathways, or to an end-stage differentiated cell, which is characteristic of a specific tissue type, and may or may not retain the capacity to proliferate further. Vascular endothelium, mural smooth muscle and erythrocytes are examples of terminally differentiated cells.

As mentioned hereinabove, individual undifferentiated ES cells are cultured in a manner suitable for inducing differentiation into vasculogenic progenitor cells. The undifferentiated ES cells utilized by the method of the present invention can be mammalian embryonic stem cells obtained from fresh or cryopreserved embryonic cell masses, cells from in-vitro-fertilized embryonic cell masses and/or cultured ES cell lines. The ES cells may be of human or non-human origin.

As is clearly demonstrated in the Examples section hereinbelow, the methods and compositions of the present invention are suitable for use with human embryonic stem cells. Since establishment of methods for manipulation and control of human embryonic stem cell differentiation is a primary goal of current medical and scientific effort, in a preferred embodiment of the present invention, the undifferentiated ES cells are human ES cells. Preferably, the ES cells are unaggregated cells, as described in detail in the Examples section hereinbelow.

According to another preferred embodiment of the present invention, differentiation of the individual undifferentiated ES cells is effected by culturing such cells on plates coated with an adhesive substrate such as type IV collagen, laminin or gelatin to prevent aggregation of the ES cells, seeding the cells at a concentration between $2 \times 10^4$ and $1 \times 10^5$ cells/cm$^2$, and providing differentiation medium. In a most preferred embodiment, individual undifferentiated ES cells are grown on type IV collagen-coated plates (available from, for example, Cell Cultureware, BD-Falcon, Boston, Mass.). See Examples section for further description of conditions for differentiation of ES cells.

One important feature of the present methodology is the cell seeding step. While reducing the present invention to practice, it was observed that a 3-dimensional embryoid body structure was not required, as had been previously contended, for mesodermal differentiation of human embryonic stem cells. Undifferentiated hES cells removed from their feeder layer and plated as single cells on type IV collagen with differentiation medium exhibited expression of indicators of endothelial differentiation (FIGS. 1A–G). Cell seeding concentration dramatically affected the efficiency of the present methodology: cells seeded according to prior art studies with mouse ES (Yamashita, J et al Nature 2000; 408:92) were not viable; such high concentrations ($1.0$–$1.5 \times 10^5$ cells/cm$^2$) of hES cells resulted in a heterogeneous population. Lower cell seeding concentrations ($5 \times 10^{4}$–$1 \times 10^{5}$ cells/cm$^2$) produced a defined population of cells, including a majority of small, flat endothelial-like cells and fewer large, smooth-muscle-like cells (FIG. 1B).

The Examples section which follows provides further description of methods of culturing "individual undifferentiated ES cells" under non-aggregating conditions.

As used herein, the term "differentiation medium" refers to a suitable medium capable of supporting growth and differentiation of the ES cells. Examples of suitable differentiation media which can be used with the present invention include a variety of growth media prepared with a base of alpha MEM medium (Life Technologies Inc., Rockville, Md., USA) or Dulbecco's minimal essential medium (DMEM) supplemented with 10% FBS (HyClone, Logan, Utah, USA) and 0.1 mM β-mercapoethanol (Life Technologies Inc., Rockville, Md., USA).

As is mentioned hereinabove it was observed that culturing of the undifferentiated ES cells as detailed hereinabove produces a defined population of cells, including a majority of small, flat endothelial-like cells and fewer large, smooth-muscle-like cells (FIG. 1B).

While previous techniques for selection of specific lineage progenitors have depended on immunodetection of indicators of differentiation and specific cell lineages and fluorescent or magnetic cell sorting (see, for example, International Patent Application WO 0210347 A2 to Benvenisty, U.S. Pat. No. 6,280,718 to Kaufman, D S and Thomson, J A; International Pat. Application No. WO0129206 A1 to Cibelli, J et al), these methods are cumbersome and costly. The observed morphological features of the mixed population of cells generated according to the teachings of the present invention enabled a simple and rapid isolation of vasculogenic progenitor cells therefrom. As is illustrated in the Examples section which follows, selection of cells smaller than 50 μm, enables rapid and efficient isolation of vasculogenic progenitor cells from the mixed population of cells (FIGS. 1C–F).

Thus, the present methodology employs a step of size/morphology selection following differentiation. Such size/morphology selection can be effected using various filtration, morphometry and/or densitometry approaches as is further described below.

Methods of filtration are well known in the art, such as the passage through a mesh, sieve, filter and the like. Filters can comprise a fibrous matrix or porous material. Such filters may be one of several commercially available filters including but not limited to cell culture filters from Pall Life Sciences (Ann-Arbor Mich., USA) or BD-Falcon (Boston, Mass., USA). A preferred filter is a nylon mesh filter having a pore size of 40 μm (Cell Cultureware, BD-Falcon, Boston, Mass.), allowing the smaller, endothelial-like cells to pass and the larger, smooth-muscle like cells to be excluded.

"Morphometry" refers to the measurement of external form, and can employ methods including but not limited to 2- and 3-D image analysis. Advanced imaging analysis software suitable for identification and isolation of cells smaller than 50 μm is commercially available to one skilled in the art [see, for example, Metamorph Software (Universal Imaging Corp., Downing Pa., USA), Imagic-5 (Image Science Software, Berlin, Germany) and Stereologer (Systems Planning and Analysis, Inc., Alexandria, Va., USA)] and can be combined with well known light microscopy and flow sorting techniques for selection of objects of desired external characteristics (e.g. size) (for suitable apparatus see, for example, U.S. Pat. No. 6,249,341 to Basiji et al). "Densitometry" refers to measurement of the optical or physical density of an object. Since the smaller, endothelial-like cells have a unique and characteristic distribution of cell components, densitometric measurements may be used to characterize and provide criteria for separation and isolation of cells. Devices suitable for densitometric isolation of endothelial-like cells are, for example, the MECOS-C1 blood cell densitometry analyzer (MECOS Co., Moscow, Russia). Cells may also be separated by sedimentation through a preparative density gradient such as FICOLL™ or PERCOLL™ (Amersham Biosciences, Inc. Piscataway, N.J. USA) (for exhaustive review of densitometric fractionation techniques, see Pertoft, H J Biochem Biophys Methods 2000; 44:1–30). Thus, the present invention provides an easy and rapid approach to progenitor cell generation and isolation. Previous methods of isolating such progenitor cells have produced progenitor populations which lack desirable proliferation capabilities, limiting their practical application (Reubinoff, B E et al Nat Biotech 2000; 18:399–404, and Schuldiner, M et al PNAS USA 2000; 97:11307–312). The vasculogenic progenitor cells isolated by the methods of the present invention are capable of generating large numbers of identical cells by proliferation through numerous cell doublings.

The population of vasculogenic progenitor cells isolated according to the teachings of the present invention is characterized by an abundance of cells expressing the endothelial progenitor marker VE-cadhedrin (FIGS. 1C–E) and endothelial markers (FIG. 1F), and actively proliferating, as indicated by incorporation of (BrdU) into the nucleus (FIG. 1I). In the absence of additional stimulus for further differentiation, these cells are capable of generating large numbers of multipotent vasculogenic progenitor cells. In addition, the vasculogenic progenitor cells may be maintained in a viable state over exceedingly long periods of time by cryopreservation according to any of the methods for conditioning, storage and thawing typically employed in the art (see, for example, U.S. Pat. No. 6,140,123 to Demetriou, et al).

Due to the importance of differentiated cells in various therapeutic approaches, directed differentiation of embryonic precursor cells presents an important goal in the art of stem cell culturing. Although embryonic stem cells maintained in culture often undergo spontaneous differentiation (Thomson J. A. et al Science 1998; 282:1145–47), directed differentiation of embryoid body-derived cells (Shamblott M J et al PNAS USA 2001; 98:113–18) and human ES cells in coculture with MEF cells (Kaufman DS et al PNAS USA 2001; 98:10716–721) has been demonstrated by manipulation of environmental factors. For example, Kaufman et al induced hematopoietic differentiation in human ES cells by culture with mouse bone marrow stromal cells (Kaufman D S et al PNAS USA 2001; 98:10716–721, and U.S. Pat. No. 6,280,718 to Kaufman, D et al) and Carpenter (US Pat Application No. 20020039724 A1) induced neuronal and glial cell development in neural progenitor cells by exposure to a cAMP activator and/or neurotrophic growth factor. Benvenisty produced pulsating cardiac muscle cells and neuron-like cells by exposing human embryoid body cells to a variety of growth factors (Itskovitz-Eldor, J et al Mol Med 2000; 6:88–95, Schuldiner, M et al PNAS USA 2000; 97:11307–312 and International Pat Application No. WO 0210347 A2 to Benvenisty N). However, all of the above-mentioned methods employ either coculturing, embryoid body formation or selection of progenitors by immunodetection of cell-surface markers.

Directed differentiation of the vasculogenic progenitor cells of the present invention can be effected by exposure to specific vascular, smooth muscle or hematopoietic growth factors.

As is illustrated in the Examples section which follows, exposure of the vasculogenic progenitor cells seeded at a low concentration, to growth factors, induces differentiation into specific mature cell phenotypes. Exposure to the growth factor hVEGF induced the appearance of both morphological and functional indicators of endothelial cell phenotype (FIGS. 1C–F and 2F–H), while exposure to the smooth muscle growth factor hPDGF-BB upregulated smooth muscle cell markers (FIGS. 2A–E). Similarly, exposure to cytokines stimulated hematopoietic differentiation of the vasculogenic progenitor cells (FIGS. 2K–M).

Thus, according to another aspect of the present invention there is provided a method of preparing somatic cells from the population of vasculogenic progenitor cells of the present invention, the method is effected by obtaining a population of vasculogenic progenitor cells as described hereinabove, and culturing the population of vasculogenic progenitor cells in the presence of at least one growth factor suitable for inducing somatic cell differentiation.

As used herein, the term "somatic cell" refers to a cell of definite lineage, identifiable as belonging to a specific cell phenotype via morphological, immunological, biochemical and/or functional criteria. Somatic cells are by definition more differentiated, and less multipotent, than progenitor and stem cells. Examples of somatic cells, in the context of the present invention, are endothelial cells, smooth muscle cells, and blood cells.

Numerous growth factors have been implicated in the complex processes of vasculogenesis, angiogenesis and hematopoietic differentiation (for reviews, see Carmeliet, P Nature Med 2000; 6:389–95, and Yancopoulos G Nature 2000; 407:242–48). Although some (i.e. VEGF, Ang and PDGF) are more dominant in their effects than others, effective differentiation of progenitor cells into somatic cells is typically a result of the combined, and temporally coordinated action of a number of factors.

Thus, according to one embodiment of this aspect of the present invention, directed differentiation is effected by using one or more growth factors including, but not limited to, vascular endothelial growth factor (VEGF), angiopoietin (Ang), platelet derived growth factor (PDGF), ephrin (Eph), fibroblast growth factor (FGF), tumor growth factor (TGF), placental growth factor (PIGF), cytokines, erythropoietin, thrombopoietin, transferrin, insulin, stem cell factor (SCF), Granulocyte colony-stimulating factor (G-CSF) and granulocyte-macrophage colony stimulating factor (GM-CSF).

Such factors are commercially available to one skilled in the art, in preparations suitable for use in cell culture.

Furthermore, it will be appreciated that the abovementioned growth factors may comprise families of factors including related molecules having different, and divergent roles in the developmental process. Thus, exposure to members of the VEGF family (for example VEGF-A, VEGF-B . . . VEGF-D), GM-CSF and bFGF may stimulate endothelial differentiation, while the PDGF and Ang families are important in smooth muscle development and lumen formation, respectively.

While reducing the present invention to practice, it was revealed that following initial exposure to differentiation medium and size selection by filtration, the vasculogenic progenitor cells, and not the smooth muscle progenitors of the present invention demonstrate robust nuclear uptake of BrdU, indicating cell proliferation.

Thus, according to another aspect of the present invention, there is provided a cell culture comprising a population of vasculogenic progenitor cells being sustainable in a proliferative, undifferentiated state for as long as 14 days or more and being capable of differentiation into smooth muscle, endothelial and/or hematopoietic cells upon exposure to at least one angiogenic, vasculogenic or hematopoietic growth factor, as detailed hereinabove. Thus, the cell culture of the present invention can be expanded and maintained in a relatively undifferentiated state.

The pluripotent, and proliferative character of embryonic and adult stem cells has naturally been exploited for the benefit of in vitro tissue preparation and engineering. In tissue engineering, tissue progenitors or precursors are cultured in vitro with appropriate differentiation factors, to achieve not only differentiation on the level of the individual cells, but also morphological, biochemical and anatomical organization into recognizable and functional tissue and organ structures, which may be used as a source for tissue/organ grafts, for artificial organ support, or organ-bioreactors. Examples of tissues that have been engineered in vitro are cartilage (Koch R J and Gorti G K Facial Plast Surg 2002; 18:59–68), skin (Lee K H Yonsei Med J 2000; 41:774–79), genitourinary tissues (Atala A Curr Opin Urol 1999; 9:517–26) and pancreatic islets (Maria-Engler S S et al Braz J Med Biol Res 2001; 34:691–7). However, these tissues have been engineered from differentiated tissue components, not from stem cells. Embryonic stem cells have been used to produce functional pancreatic islet-like structures (Lemelsky, et al Science 2001; 292:1389–94) and blood tissue (Kaufman D S et al PNAS USA 2001; 98:10716–21) in vitro.

Vessel-like structures have also been formed in vitro. Kaushal et al (Nat Med 2001; 7:1035–40) reported peripheral endothelial progenitors forming functional neovessels on decellularized porcine vessels. Levenberg et al (PNAS USA 2002; 99:4391–96), working with human embryoid body derived endothelial cells, demonstrated formation of tube-like structures in matrigel, and microvessels upon transplantation. However, these vessel-like structures typically lack the normal complex vascular/mural organization characteristic of normal blood vessels.

While reducing the present invention to practice, it was surprisingly uncovered that the vasculogenic progenitor cells of the present invention form small, capillary-like vessels when grown in matrigel with appropriate growth factors (FIGS. 3A–G), and larger vascular structures on alginate scaffolds (FIGS. 4A and 4B). In both cases, normal endothelial and mural organization were observed (FIGS. 3E–G and 4A–B), as well as blood cell formation within the vascular structures.

Thus, according to another aspect of the present invention, there is provided a method for preparing vascular tissue. The method is effected by culturing the population of vasculogenic progenitor cells of the present invention in the presence of at least one vasculogenic and/or angiogenic growth factor, under conditions suitable for inducing vascular tissue differentiation.

According to one embodiment of this aspect of the present invention, vascular tissue is prepared by culturing the vasculogenic progenitor cells in a semi-solid, vascularization-promoting medium. Such a medium typically comprises extracellular matrix components (for example, Matrigel- B D Biosciences, Bedford, Mass. USA) or collagen (e.g. rat tail collagen I), in which growth factor-treated, differentiating vasculogenic cells are mixed following aggregation. The growth factors may be any of the abovementioned vasculogenic and/or angiogenic factors, such as vascular endothelial growth factor (VEGF), angiopoietin (Ang), platelet derived growth factor (PDGF), ephrin (Eph), fibroblast growth factor (FGF), tumor growth factor (TGF) and placental growth factor (PlGF), known to induce vasculogenic and/or angiogenic growth or development. In a preferred embodiment, the growth factors are 50 ng/ml $VEGF_{165}$ and 10 ng/ml hPDGF-BB. Growth of vascular structures is typically evident after 7–15 days incubation. Characteristic endothelial cell components, such as Weibel-Palade bodies and lipoprotein capsules; vessel lumen, and blood cells are detected by histology and electron microscopy, as detailed in the Examples section which follows. Complex macroscopic tissue architecture may also be mimicked in vitro by seeding the progenitors of the present invention on a porous support, or scaffold. Such supports are well known in the art (see U.S. Pat. Nos. 5,759,830 and 5,770,417 to Vacanti et al, and U.S. Pat. No. 6,379,962 to Holy et al), and have been recently proposed, for example, as tubular blood vessel prostheses for vascularization and epithelialization by host cells, for vascular regeneration (U.S. Pat Application 20020019663 A1 to Termin, PL et al), for wound repair with fibroblasts (U.S. Pat Application 20020076816 to Dai, J et al) and for in vitro bone engineering (U.S. Pat Application No. 20020028511 to deBruijn, J D et al). In one embodiment of the present invention, vascular tissue of greater than capillary size is prepared by culturing the vasculogenic progenitor cells on a 3-dimensional scaffold. In a preferred embodiment, the scaffold is a porous, biodegradable sponge-like material such as poly-L lactic acid, polylactic-glycolic acid or alginate, and differentiation medium contains growth factors $VEGF_{165}$ (50 ng/ml) and hPDGF-BB (10 ng/ml). Vascular tissue of the present invention grown on such an alginate scaffold typically demonstrates vascular characteristics such as lumen, endothelial and smooth muscle cells, cell inclusions and von Willebrand Factor at 14 days in culture (FIGS. 4A–B).

Living vascular tissue prepared by the method of the present invention can be used for regenerative therapy, and for neovascularization of non-vascular tissue. Vascular tissue may be implanted into embryonic, growing or adult organisms suffering from insufficient or faulty vascularization, as in the microvascular pathology of diabetes, or into tissues experiencing, or at risk of ischemic damage, as in ischemic heart disease and cerebral-vascular disease. Similarly, vascular tissue of the present invention can provide blood vessels of large diameter for tissue replacement therapy in cases of surgical bypass, vascular degeneration such as atherosclerosis and autoimmune disease.

It will be appreciated that differentiating cultures or vascular tissues prepared from vasculogenic progenitor cells of the present invention also provide a model suitable for the investigation of processes effecting vascular development and function. For example, the cells and tissues of the present invention may be cultured in the presence of suspected toxic materials, antibodies, teratogens, drugs and the like, or exposed to non-standard environmental factors such as temperature, gas partial pressure and pH, or co-cultured in the presence of cells from other tissues or other organisms. Changes in parameters of growth and development, such as failure or delay of endothelial marker expression, loss of proliferative capacity, or dis-organization of in vitro vascularization can be assessed to determine the effect of various factors.

Thus, according to another aspect of the present invention, there is provided a method of determining an effect of a factor on vascular development, growth and/or modification. The method is effected by exposing the population of vasculogenic progenitor cells of the present invention to the factor, and determining an effect of the factor on the cells.

The vasculogenic progenitor cells can be exposed to a factor suspected of inhibiting or downregulating vascular development, growth or modification. Such assays are well known in drug development and research, and may be employed to test undesirable side effects of substances intended for the treatment of other, non-vascular processes, or, alternatively, may be used to discover novel inhibitors of vasculogenesis. In order to enable assessment of effects inhibiting vascular development and growth, conditions of culturing the vasculogenic progenitor cells should be favorable, or more preferably, optimal, for vasculogenesis and angiogenesis. This includes optimization of medium components (such as growth or differentiation factors), temperature, substrate composition, gas partial pressures and the like, for the specific stage of vascular development being investigated.

Indeed, while reducing the present invention to practice, the present inventors found that incubation of vasculogenic progenitor cells of the present invention with an angiogenesis-inhibiting anti VE-cad mAb prevented differentiation by hVEGF (FIGS. 5A–B). Similarly, a drug intended for treatment of early complications of pregnancy could be screened for potential harmful effects on embryonic vascular development, by exposing vasculogenic progenitor cells, removing the drug and monitoring modulation of growth or development of the cells by methods commonly used in the art. Similarly, factors stimulating or upregulating angiogenesis and/or vasculogenesis in the vasculogenic progenitor cells can be best assessed under sub-optimal conditions of culturing. Substances affecting vasculogenesis and/or angiogenesis include peptides, peptidomimetics, polypeptides, antibodies, chemical compounds and biological agents.

Since progenitor cell populations are highly amenable to tissue engineering, transplantation and regenerative therapy, genetic manipulation of such cells can provide a source of developing cell populations bearing unique, previously unattainable characteristics.

As is clearly illustrated in Example 1 of the Examples section hereinbelow, the vasculogenic progenitor cell population of the present invention exhibits active proliferation thus making such cells amenable to genetic manipulations rendering such cells, for example, capable of expressing at least one exogenous polypeptide. Exogenous polypeptides expressed in such a cell culture can be cell surface markers, cell-surface antigens, angiogenic factors, vasculogenic factors and hematopoietic factors. Additional polypeptides that can be expressed are, for example, various receptors, ligands, cell adhesion molecules, enzymes, peptide hormones and immune system proteins.

The vasculogenic progenitor cells of the present invention may be manipulated to express exogenous polypeptides by introduction of a nucleotide sequence encoding the exogenous polypeptide, or a precursor form of the exogenous polypeptide. Exogenous foreign nucleic acid sequences can be transferred to the vasculogenic progenitor cells of the culture by electroporation, calcium phosphate, microinjection, lipofection, retro- or other viral or microbial vector or other means well known to one of ordinary skill in the art. Preferably, expression of the exogenous sequence(s) is inducible. Cells expressing the exogenous polypeptide may be screened and isolated by techniques well known in the art including, but not limited to immunoblotting, immunofluorescence, ELISA and RT-PCR. Cells expressing exogenous polypeptides can be harvested, expanded, differentiated and used for, for example, repairing or augmenting a defect. In this manner, cells, tissues or organs can be prepared with exogenous major histocompatability antigens which will decrease rejection of transplanted materials by the host organism. In addition, cells expressing and secreting vasculogenic growth factors, or overexpressing growth factor receptors can be selected and cultured, creating cultures of vasculogenic progenitor cells with altered temporal dynamics and/or sensitivities to differentiation factors.

The vasculogenic progenitor cells isolated by the methods of the present invention can be used therapeutically, in treatment of vascular and vascular related disease. Potential applications include cell transplantation for repair of damaged and ischemic tissues, vascularization of regenerating tissue and embryonic regenerative medicine. Examples of such therapeutic applications of stem and progenitor cells are the augmentation of vessel growth observed in areas of ischemic tissue after implantation of adult endothelial progenitors (Kawamoto A et al Circulation 2001; 103:634–37) and the neovascularization by adult endothelial progenitors following cerebral ischemia in induced stroke in mice (Zhang Z G et al Circ Res 2002; 90:284–88).

Thus, according to yet another aspect of the present invention there is provided a method of relieving or preventing a vascular disease or condition in a mammalian subject. The method is effected by administering the vasculogenic progenitor cells of the present invention to the subject.

Methods of administering the progenitor cells of the present invention to subjects, particularly human subjects include injection or implantation of the cells into target sites in the subjects, the cells of the invention can be inserted into a delivery device which facilitates introduction by, injection or implantation, of the cells into the subjects. Such delivery devices include tubes, e.g., catheters, for injecting cells and fluids into the body of a recipient subject. In a preferred embodiment, the tubes additionally have a needle, e.g., a syringe, through which the cells of the invention can be introduced into the subject at a desired location. The progenitor cells of the invention can be inserted into such a delivery device, e.g., a syringe, in different forms. For example, the cells can be suspended in a solution or embedded in a support matrix when contained in such a delivery device. As used herein, the term "solution" includes a carrier or diluent in which the cells of the invention remain viable. Carriers and diluents which can be used with this aspect of the present invention include saline, aqueous buffer solutions, solvents and/or dispersion media. The use of such carriers and diluents is well known in the art. The solution is preferably sterile and fluid to the extent that easy syringability exists. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the invention can be prepared by incorporating progenitor cells as described herein in a carrier or diluent and, as required, other ingredients enumerated above, followed by filtered sterilization.

Support matrices in which the vasculogenic progenitor cells can be incorporated or embedded include matrices which are recipient-compatible and which degrade into products which are not harmful to the recipient. Natural and/or synthetic biodegradable matrices are examples of such matrices. Natural biodegradable matrices include plasma clots, e.g., derived from a mammal, polymeric scaffolds, matrigel and collagen matrices. Synthetic biodegradable matrices (scaffolds) include synthetic polymers such as polyanhydrides, polyorthoesters, and polylactic acid. Other examples of synthetic polymers and methods of incorporating or embedding cells into these matrices are known in the art. See e.g., U.S. Pat. Nos. 4,298,002 and 5,308,701. These matrices provide support and protection for the fragile progenitor cells in vivo and are, therefore, the preferred form in which the vasculogenic progenitor cells are introduced into the recipient subjects.

Differentiation of the implanted vasculogenic progenitor cells of the invention may be directed by factors originating from the surrounding tissue, or may be initiated by pre-implantation incubation with lineage-specific growth factors. Thus, for example, defects requiring regeneration of smooth muscle can be treated with cells having been exposed to PDGF-BB, to achieve a population enriched in smooth muscle precursors.

Vascular disease and conditions that can be treated with the methods of the present invention include congenital and acquired vascular disorders and ischemia/reperfusion injury. As used herein, the term "congenital vascular disorders" refers to vascular disorders existing from birth, including both hereditary and developmental disorders. "Acquired vascular disorders" refers to vascular disorders ensuing after birth, including secondary vascular manifestations of systemic or other disease, such as the microvascular pathologies of diabetes. "Ischemia/reperfusion injury" refers to cell or tissue injury resulting from interrupted or diminished blood supply, and the tissue damage, especially the inflammatory response, associated with reestablishing circulation in ischemic tissues.

Conditions which may benefit from such treatment include ischemic conditions (associated, for example, with myocardial, brain or peripheral vascular ischemia), wound healing, tissue grafting (including transplant) and conditions involving endothelial cell growth and proliferation, for example after coronary angioplasty, stenting or related procedures, re-endothelialization of arterial grafts, and endothelial regeneration in A–V shunts, e.g. in renal dialysis patients. In view of the complications encountered using porcine progenitor xenografts in primates (Buhler L et al Transplantation 2000; 70:1232–31) the methods of the present invention, which can be applied to human stem cells, are especially suited for treatment of such vascular conditions.

Since it was observed herein that the vasculogenic progenitor cells of the invention, when exposed to hematopoietic growth factors and cytokines, can be induced to differentiate into blood cell progenitors and mature blood cells (FIGS. 2K–M and 3D–F, respectively), the vasculogenic progenitor cells of the invention can also be used for treating or preventing a hematological disease or condition in a mammalian subject.

Such treatment can be effected by administering the cells into a subject under conditions suitable for stimulating differentiation into both endothelial and blood cells. Hematological diseases or conditions that can be treated or prevented in this manner include congenital and acquired blood disorders, clotting disorders and neoplastic disease.

One example of a clotting disorder suitable for treatment by the method of the present invention is von Willebrand's disease, a type of hemophilia caused by deficiency in the endothelial von Willebrand clotting factor. While reducing the present invention to practice, it was uncovered that differentiated endothelial cells prepared by the methods of the present invention contain von Willebrand factor (FIGS. 3A–G and 4A–B). Thus, endothelial cells or endothelial progenitor cells of the present invention, or compositions thereof can be administered, producing the clotting factor and alleviating the clotting deficiency.

In addition to the abovementioned therapeutic applications, vasculogenic progenitor cells isolated and prepared by the methods of the present invention can be used to provide vascularization of non-vascular, or inherently poorly vascularized tissue. It will be appreciated that one of the most important challenges facing the field of tissue engineering is the adequate perfusion of tissue and organs prepared in vitro for implantation. To date, most tissue engineering methods have relied on microporous supports and vascularization from the host to provide permanent engraftment and transfer of oxygen and nutrients, with varying and often unpredictable results, especially where thick, complex tissues (e.g. liver) are concerned. One alternative approach is the fabrication of "vascular" channels in silicon by micromachining, for population by mixed hepatocytes and endothelial cells in vitro (Kaihara S et al Tissue Eng 2000; 6:105–07). In another approach more closely mimicking normal development, endothelial cells have been cocultured with skin (Black A F et al Cell Biol Toxicol 1999; 15:81–90) or adipose (Frerich B et al Int J Oral Maxillofac Surg 2001; 30:414–20) cells to provide a vascular network for the growing tissue. However, none have been successful in engineering viable, implantable vascularized tissues.

Thus, according to a further aspect of the present invention, there is provided a method of vascularizing a mammalian tissue. The method is effected by obtaining a population of vasculogenic progenitor cells and contacting the cells with a mammalian tissue under conditions suitable for differentiation of the vasculogenic progenitor cells into endothelial and smooth muscle cells. In one preferred embodiment, the mammalian tissue is an engineered, non-vascular tissue.

Examples of such engineered tissue are masses of in vitro prepared hepatocytes, epidermal and dermal cells, pancreatic and bone cells for implantation. Contacting the tissue with the differentiating vasculogenic progenitor cells can be by coculture in semisolid matrix or on a porous scaffold, as is commonly used in engineered tissue architecture, as detailed hereinabove. Contacting the mammalian tissue can be performed in vitro, prior to implantation into the host organism, or in vivo, into a previously implanted or existing tissue. In another preferred embodiment, the mammalian tissue is an embryonic tissue, prepared for implantation into adult host organism, or for implantation and growth as an embryo.

While reducing the present invention to practice, it was also observed that the cells larger than 50 µm retained by the size selection step of the present methodology comprise a population enriched in smooth muscle cells precursors, expressing characteristic epithelial cell markers and morphology (FIGS. 1H and 1G, respectively).

Thus, the present invention also provides a method of preparing epithelial progenitor cells from undifferentiated ES cells. The method is effected by culturing the undifferentiated ES cells in a manner suitable for differentiation into vasculogenic progenitor cells and isolating cells larger than 50 µm. Conditions for culture of the epithelial precursors, and their differentiation into smooth muscle cells, were substantially similar to those detailed herein for the vasculogenic progenitor cells, with substitution of smooth muscle or epithelial growth factors, such as PDGF-BB, in place of endothelial or vasculogenic growth factors. However, it was noted that the epithelial and smooth muscle cells lack the proliferative capacity of the smaller, vasculogenic progenitor cells.

Adult vascular tissue is comprised of endothelial and epithelial cells, distinguishable by size, morphology and cell markers, as well as location and function. Current methods for the isolation of vascular cell types rely upon cell surface marker detection, immunofluorescence and flow cytometry (see, for example, Kevil E G and Bullard D C Acta Physiol Scand 2001; 173:151–57), making the preparation of vascular cells for experimentation and primary culture cumbersome, expensive and inefficient. Thus, it will be appreciated that the methods of the present invention may be employed to isolate and prepare cells from vascular tissue, as well as from undifferentiated stem cells. In a preferred embodiment, the cells of the vascular tissue are dissociated by mechanical, or enzymatic means, such as trypsin or collagenase digestion, to obtain a mixed population of dissociated cells, and the smaller (smaller than 50 µm) endothelial cells isolated by size selection as detailed herein for the vasculogenic progenitor cells. Similarly, adult epithelial cells can be isolated from vascular tissue by a similar method, wherein the retained cell population (greater than 50 µm), rich in epithelial cells, is collected.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I–III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1–4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I–III Cellis, J. E., ed. (1994); "Current Protocols in Immunology" Volumes I–III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1–317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Materials and Methods

Cell Culture

Undifferentiating human embryonic stem (hES) cells (H9.2, H13) were grown on inactivated mouse embryonic feeder layer (MEF) as previously described (Amit M, et al. Dev Biol 2000; 227: 271–78), in 80% knock-out DMEM medium (no pyruvate, high glucose formulation; Life Technologies Inc., Rockville, Md. USA) supplemented with 20% FBS (HyClone, Logan, Utah, USA), or serum replacement and bFGF, 1 mM L-glutamine, 0.1 mM mercaptoethanol, and 1% nonessential amino acid stock (Life Technologies Inc., Rockville, Md., USA). hES cells were removed from the feeder layer using EDTA 5 mM supplemented with 1% fetal bovine serum (FBS; HyClone, Logan, Utah, USA) and dispersed to single-cells using a 40 µm mesh strainer (Benton, Dickinson and Co, Discovery Labware, Bedford, Mass., USA).

For differentiation, undifferentiated hES single cells were plated on type IV collagen-coated (Becton Dickinson and Co, San Jose, Calif., USA) or 0.1% gelatin-coated (Sigma Chemical Co., St Louis Mo., USA) 6-well dishes at a concentration of $5 \times 10^4$ cells/cm$^2$, in differentiation medium consisting of alpha MEM medium (Life Technologies Inc., Rockville, Md., USA) supplemented with 10% FBS (HyClone, Logan, Utah, USA) and 0.1 mM β-mercapoethanol (Life Technologies Inc., Rockville, Md., USA). On day 6 of culture cells were filtered through a 40 µm mesh strainer (Becton, Dickinson and Co, Discovery Labware, Bedford, Mass., USA) and were analyzed or recultured for further differentiation. For reculture, the strained cells were seeded at $2.5 \times 10^4$ cells/cm$^2$ on type IV collagen coated dishes (Benton Dickinson and Co, San Jose, Calif., USA) in differentiation medium (see above) with hVEGF$_{165}$ 50 ng/ml or hPDGF-BB 10 ng/ml (both from R&D Systems Inc, Minneapolis, Minn., USA) for an additional 10–12 days.

Collagen Gel and Matrigel 3-D Vascularization Assays

Before three dimensional culture, filtrated cells cultured for 6 days in differentiation medium were harvested with EDTA 5 mM and 0.3–0.5×10$^6$ cells per ml were incubated in differentiation medium containing 50 ng/ml VEGF$_{165}$ and hPDGF-BB 10 ng/ml on uncoated petri dishes (Ein-Shemer Industries, Israel) for maximum of 24 hours to induce aggregation. For the collagen gel assay, aggregates were resuspended in 2× differentiation medium and mixed with an isovolume of rattail collagen I (3 mg/ml) (F.Hoffman-La Roche Ltd, Basel, Switzerland). Initially, 250 µl of this mixture was plated in 24-well dishes, which was allowed to polymerize for 15 min at 37° C., before adding 500 µl of differentiation medium supplemented with the same growth factors. For the Matrigel assay, 24-well dishes were coated with 380 µl of Matrigel (Becton Dickinson and Co, San Jose, Calif., USA), incubated 30 min at 37° C., and aggregates were seeded on the matrigel in differentiation medium containing hVEGF (50 ng/ml) and hPDGF-BB (10 ng/ml). In some assays, aggregates were resuspended within the Matrigel (Becton Dickinson and Co, San Jose, Calif., USA), incubated for 30 min at 37° C., and then added to the wells with differentiation medium containing hVEGF (50 ng/ml) and hPDGF-BB (10 ng/ml). For all assays, cells were incubated for 7–12 days and analyzed using contrast-phase microscope (Olympus Optical Co Ltd, Hamburg GmbH).

Scaffold Vascularization

LF120 50 µl alginate scaffold (Shapiro L and Cohen S. Biomaterials 1997; 18: 583) was kindly provided by Prof Smadar Cohen (Ben Gurion University, Beer Sheba, Israel). As described above, the scaffolds were seeded with 24 hour old ESH cell aggregates prepared as described hereinabove; approximately 0.5–1.0×10$^6$ cells were seeded per scaffold. The cell-containing scaffolds were then cultured in differentiation medium supplemented with 50 ng/ml VEGF$_{165}$ and 10 ng/ml hPDGF-BB.

Hematopoietic Colony Assay

Hematopoietic progenitor capability was demonstrated by seeding filtrated, VEGF-treated, VE-cad+ ESH cells, as single cells, 1–2×10$^5$ cells per plate, in semisolid media supplemented with cytokines (Methocult GF+ media; Stem-Cell Technologies, Vancouver BC) (for details of the assay, see Kaufman D S et al, PNAS 2001; 98:10716–21). After 14 days incubation, the plates were scored for colony-forming units (CFU), according to standard criteria [Eaves C and Lambie, K Atlas of Human Hematopoietic Colonies (1995); StemCell Technologies, Vancouver, BC].

Immunostaining, Dil-Ac-LDL and BrdU Incorporation

Cultured cells were fixed in situ by incubation with 4% paraformaldehyde (Sigma-Aldrich Corp., St Louis, Mo., USA) in phosphate buffered saline (PBS) (Life Technologies Inc., Rockville, Md., USA) for 30 min at room temperature. After washing with PBS, cells were stained according to suppliers instructions with relevant primary antibodies: goat anti human KDR (R&D Systems Inc, Minneapolis, Minn., USA), mouse anti hCD31, mouse anti hSMA, mouse anti hCalponin, mouse anti h Smooth muscle myosin heavy chain (all from DAKO Corp, Carpenteria, Calif., USA), goat anti human VE-Cadherin (Santa Cruz Biotechnology, Inc., Santa Cruz, Calif., USA), (DAKO Corp, Carpenteria, Calif., USA), mouse anti Smoothelin (CHEMICON, Intn'l, Inc. Temecula, Calif., USA). Controls consisted of cells incubated with secondary antibodies alone. Immunostained cultures were examined and photographed using fluorescence microscopy (Olympus Optical Co, Ltd. Hamburg, GmbH).

For uptake of Dill-labeled ac-LDL, cultured ESH cells were incubated with 10 µg/ml Dill-labeled ac-LDL (Biomedical Technologies Inc., Stoughton, Mass., USA) for 4 h at 37° C. Following incubation, cells were washed 3 times with PBS, fixed with 4% paraformaldehyde for 30 minutes, examined and photographed using a fluorescent microscope (Olympus Optical Co, Ltd. Hamburg, GmbH).

BrdU incorporation in ESH cultures and differentiating cells was examined using a BrdU staining kit (Zymed Labs Inc., South San Francisco, Calif., USA) in-situ, according to manufacturers instructions. Briefly, BrdU solution was diluted 1:100 in culture medium and added to the cells overnight, followed by two PBS washes, fixation with 75% ethanol and specific BrdU immunostaining.

Immunophenotype

Cells were characterized using immunofluorescence staining as previously described (Reubinoff B E et al., Nat Biotech 2001; 19: 1134). Briefly, filter-separated ESH cells were recultured, as described above, in differentiation medium (alpha MEM, 10% FBS and 0.1 β-mercaptoethanol) on type IV collagen plates for 12–20 hours, fixed and assayed for expression of specific cell-type markers with anti human VE-Cadherin (Santa Cruz Biotechnology, Inc., Santa Cruz, Calif., USA), and anti human KDR (R&D Systems Inc, Minneapolis, Minn., USA). At least one hundred and fifty cells were scored within random fields (×100) for the expression of each of these markers, and experiments were repeated at least three times.

Histolomorphology and Immunohistochemical Analysis

Matrigel or collagen gel containing cells (as describe for the Collagen gel and Matrigel 3-D vasculanization assays hereinabove) were plated as described above onto glass cover slips, in 24-well dishes. Upon completion of treatments, the cell-containing gel blocks on cover slips were fixed in 10% neutral-buffered formalin, dehydrated in graduated alcohol baths (70%–100%), and embedded in paraffin. Where used, the alginate scaffolds were directly dehydrated in graduated alcohol. For general histomorphology, 1–8 µm sections were stained with hematoxylin/eosin or toluidine blue. Deparaffinized sections were immunostained with the relevant primary antibodies, using LSAB+ staining kit (DAKO Corp, Carpenteria, Calif., USA) or Cell and Tissue staining kit (R&D Systems Inc, Minneapolis, Minn., USA) according to manufacturers instructions. Stained sections were viewed and photographed microscopically at ×100–× 400 magnification.

FACS Analysis

Cells expressing the endothelial progenitor markers VEGFR2 (KDR) and VE-cad were detected and quantified from the two size-separated human ES cell populations after filtration and separate reculturing on type IV collagen, as described above. For FACS analysis, ESH filtered cells were washed in PBS containing 5% FBS, incubated with human VE-Cadherin (Santa Cruz Biotechnology, Inc., Santa Cruz, Calif., USA), or human KDR (R&D Systems Inc, Minneapolis, Minn., USA), washed, and incubated 30 min with suitable second antibodies. Cells were analyzed using a FACSCalibur (Benton Dickinson and Co, San Jose, Calif., USA) with CELLQUEST software. IN both assays, cells reacted with second antibodies only served as controls.

Electron Microscopy

Cell seeded in Matrigel or collagen gel were fixed for one hour in 3% glutaraldehyde, in 0.1M sodium cacodylate and then post-fixed in 1% OsO$_4$ in veronal-acetate buffer for 1 hour. Preparation for electron microscopy analysis was performed according to standard procedure at the Pathology Department of the Rambam Medical Center, Haifa, Israel. Briefly, the cells were stained with lead-citrate, dehydrated and embedded in Epon resin. Sections were cut at a thickness of 600 Å using a diamond knife, examined and photographed using a JEM-100SX electron microscope.

Reverse Transcription (RT)-PCR Analysis

Total RNA was extracted from progenitors and different lineage cells using TriReagent (Sigma-Aldrich Corp., St Louis, Mo., USA) according to the manufacturer's instructions. Total RNA was quantified by UV spectrophotometry, and 1 µg was used for each RT sample. RNA was reverse transcribed with M-MLV Reverse Transcriptase (Promega Corp., Madison, Wis., USA) and oligo (dT) primers (Promega Corp., Madison, Wis., USA) according to manufacturer's instructions. PCR amplification of the selected transcripts was done with BIOTAQ™ DNA Polymerase (BIOLINE, Ltd GmbH Luckenwalde, Germany) using 1 µl of RT product per reaction, according to manufacturers instructions. In some cases $MgCl_2$ concentration (normally 1.5 mM) was calibrated (indicated below). To ensure semi-quantitative results in the RT-PCR assays, the number of PCR cycles for each set of primers was verified to be in the linear range of the amplification. In addition, all RNA samples were adjusted to yield equal amplification of the housekeeping gene GAPDH as an internal standard. PCR conditions and protocol consisted of: 5 min at 94° C. (hot start); followed by 30–40 cycles (actual number noted below) of: (a) 94° C. for 30 sec; (b) annealing temperature (Ta, noted below) for 30 sec; and (c) 72° C. for 30 sec, concluding with a final 7-min extension at 72° C. at the end. Oligonucleotide-specific conditions were as follows: α-sma, 32 cycles, Ta 60° C. (Yamamura, H et al. Int. J. Cancer (Pred. Oncol.) 1998; 79: 245); calponin, 35 cycles, Ta 60° C. (Yamamura, H et al. Int. J. Cancer (Pred Oncol) 1998; 79: 245); SM-MHC, 35cycles, Ta 62° C., 1 mM $MgCl_2$ (Boreham et al. Am J Obsetet Gynycol 2001; 185:944–52); SM22α, 35 cycles, Ta 60° C. (Yamamura, H et al. Int. J. Cancer (Pred. Oncol.) 1998; 79: 245); caldesmon, 35 cycles, Ta 60° C. (Duplaa, C. et al., Circ Res. 1997; 80:159); GATA2, 35 cycles, Ta 55° C. (Kaufman D S et at PNAS 2001; 98:10716); AC133, 32 cycles, Ta 60° C. (Shamblott M J et at, PNAS 2001; 98:113); Tie2, 35 cycles, Ta 60° C. (Ahmad,S et al, Cancer 2001; 92:1138); CD31, 32 cycles Ta 60° C. (Quarmby, S et al Arterio Thrombo Vas Biol 1999; 19:588–97); Tall, 40 cycles Ta 53° C. (Kaufman D S et al PNAS 2001; 98:10716); GAPDH, 32 cycles, Ta 60° C. (Itskovitz-Eldor J et at Mot Med 2000; 6:88).

Oligonucleotide Primers:

For the PCR reactions the following specific oligonucleotide primers were used:

(a) α-sma: 5' CCAGCTATGTGAAGAAGAAGAGG 3' (SEQ. ID. NO: 1) (sense) and 5' GTGATCTCCTTCTGCAT-TCGGT 3' (SEQ. ID. NO: 2) (antisense). The predicted size of band is 965 base pairs;

(b) Calponin: 5' GAGTGTGCAGACGGAACTTCAGCC 3' (SEQ. ID. NO: 3) (sense) and 5' GTCTGTGCCCAACT-TGGGGTC 3' (SEQ. ID. NO: 4) (antisense). The predicted size of band is 671 base pairs;

(c) SM-MHC: 5' CTACAGGAGCATGCTGCAGGATCC 3' (SEQ. ID. NO: 5) and 5' GCTTGCAGAAGCTGCT-TCTCCAGC 3' (SEQ. ID. NO: 6), corresponding to nucleotides 579 (sense) and 758 (antisense), respectively. The predicted size of band is 179 base pairs;

(d) SM22α: 5' CGCGAAGTGCAGTCCAAAATCG 3' (SEQ. ID. NO: 7) (sense) and 5' GGGCTGGTTCTTCT-TCAATGGGG 3' (SEQ. ID. NO: 8) (antisense). The predicted size of band is 928 base pairs;

(e) Caldesmon: 5' AACAACCTGAAAGCCAGGAGG 3' (SEQ. ID. NO: 9) and 5' GCTGCTTGTTACGTTTCTGC 3' (SEQ. ID. NO: 10), corresponding to nucleotides 244 (sense) and 792 (antisense), respectively. The predicted size of band is 530 base pairs;

(f) GATA2: 5' AGCCGGCACCTGTTGTGCAA 3' (SEQ. ID. NO: 11) (sense) and 5' TGACTTCTCCTGCATGCACT 3' (SEQ. ID. NO: 12) (antisense). The predicted size of band is 242 base pairs;

(g) AC133: 5' CAGTCTGACCAGCGTGAAAA 3' (SEQ. ID. NO: 13) (sense) and 5' GGCCATCCAAATCTGTCCTA 3' (SEQ. ID. NO: 14) (antisense). The predicted size of band is 200 base pairs;

(h) Tie2: 5' ATCCCATTTGCAAAGCTTCTGGCTGGC 3' (SEQ. ID. NO: 15) (sense) and
5' TGTGAAGCGTCTCACAGGTCCAGGATG 3' (SEQ. ID. NO: 16) (antisense). The predicted size of band is 512 base pairs;

(i) CD31: 5' CAACGAGAAAATGTCAGA 3' (SEQ. ID. NO: 17) (sense) and 5' GGAGCCTTCCGTTCTAGAGT 3' (SEQ. ID. NO: 18) (antisense). The predicted size of band is 260 base pairs;

(j) Tal1: 5' ATGGTGCAGCTGAGTCCTCC 3' (SEQ. ID. NO: 19) (sense) and 5' TCTCATTCTTGCTGAGCTTC 3' (SEQ. ID. NO: 20) (antisense). The predicted size of band is 331 base pairs;

(k) GAPDH: 5' AGCCACATCGCTCAGACACC 3' (SEQ. ID. NO: 21) (sense) and 5' GTACTCAGCGGCCAG-CATCG 3' (SEQ. ID. NO: 22) (antisense). The predicted size of band is 302 base pairs.

Example 1

Isolation and Enrichment of Human Vasculogenic Progenitor Cells from Human Stem Cells Despite the overwhelming importance of human stem cell technology to research and medicine, application of discoveries made in research with non-human species to human stem cells has been painstakingly difficult, requiring great ingenuity and much effort. While murine embryonic stem cell (mES) lines, for example, retain their pluripotency in culture, and may be predictably manipulated to differentiate in vitro into cells of mesodermal, endodermal and ectodermal lineage, in vitro differentiation in human and other primate ES cell lines has been characterized by inconsistency, disorganization, and lack of synchrony, obviating successful in vitro tissue organization (see, for example, Thompson, et al Curr Top Dev Biol 1998; 38:133–165). In pursuing the isolation of vasculogenic progenitor cell from human embryonic stem cells, initial human ES mesodermal differentiation was attempted in a novel two dimensional (2D) rather than the three dimensional (3D) model commonly used in the art, based upon the observation that the 3D embryoid body structure is not required for mouse stem cell mesodermal differentiation (Nishikawa S-I., et al., Development 1998; 125:1747).

Undifferentiated human embryonic stem cell line H9.2 and H13 cells were grown as previously described (Amit M et al Dev Biol 2000; 227:271–78), removed from feeder layer and plated as single cells on type IV collagen coated dishes with differentiation medium as had been described for mouse CCE-ES cells (Yamashita J, et al. Nature 2000; 408:92). Previous experience with murine stem cells indicated that specific cell seeding concentration is crucial for induction endothelial differentiation. However, seeding human ES cells in the recommended cell concentration ($1\times10^4$ cells/cm$^2$) resulted in cell death. Therefore, several cell-seeding concentrations were investigated. Seeding the cells at higher concentrations on a variety of attachment substrates ($1.0-1.5\times10^5$ cells/cm$^2$) resulted in an inconsistent mixed population of undifferentiated and differentiating cells (data not showed). Surprisingly, seeding cells at low concentration ($5-10\times10^4$ cells/cm$^2$) on type IV collagen substrate promoted differentiation that resulted in two distinct populations of cell types (FIG. 1B). A significant proportion of the cell population comprised smaller flat cells with large nuclei resembling endothelial progenitor morphology (FIG. 1B, arrows) previously recognized in murine cells (Yamashita J, et al. Nature 2000; 408:92), while the remainder were large flat cells with obvious fibrous structure (FIG. 1B, arrowheads).

In order to separate the two cell populations, and isolate the smaller, human vasculogenic cell progenitors, the cells were filtered through a 40 μm strainer, segregating the endothelial-like cells from the large flat cells. To evaluate the proportion of endothelial progenitors in the cultures, the filtered cell populations were characterized by detection of specific cell-type markers, as previously described for monitoring the differentiation of neuron progenitors derived from hES cells (Reubinoff B B et al., Nat Biotech 2001; 19:1134). Filtrated cells were plated, fixed, and analyzed immunologically for the expression of human vascular endothelial endothelial receptor 2 (VEGFR2, KDR), and vascular endothelial cadherin VE-cad, both known to play an important role in mouse endothelial progenitor development (Nishikawa S-I., et al., Development 1998; 125: 1747).

Unexpectedly, when the expression of these markers in the two populations was quantified by immunodetection and FACS analysis (FIGS. 1C–E), a significant proportion of the smaller, endothelial-like cells were found to express VE-cad (78%, FIG. 1C) and a smaller portion expressed VEGFR2 (28%, FIG. 1C). When the smaller, filtrated cells were plated for 12 hours, fixed and analyzed for immunomorphology with fluorescent anti VE-cad antibody (FIGS. 1D–E), significantly greater expression of VE-cad was detected (90.55±5.20%), most likely due to the low fluorescent intensity observed when VE-cad is expressed at the cell-to-cell junctions (FIG. 1E). Trials of a variety of cell-seeding densities indicated optimal VE-cad expression at $5\times10^4$ cells/cm$^2$.

When further characterized by RT-PCR amplification of RNA, the endothelial-like cells were found to actively express the endothelial markers CD31 and Tie2; AC133/CD133, GATA2 and Tall, early endothelial/hematopoeitic progenitor cell markers (Peichev, M et al., Blood 2000; 95:952 and Kaufman D S et al PNAS 2001; 98:10716) (FIG. 1F, Filtrated). RT-PCR of RNA from undifferentiated human stem cells (FIG. 1F, hES) demonstrated no CD31, Tie2, Tall or GATA2 expression, and only minimal expression of AC133. Note that the intensities of the GAPDH bands are identical for both the undifferentiated and differentiated cell populations (FIG. 1F), indicating the specific nature of the change in cell phenotype with differentiation.

Immunofluorescent staining of the larger, excluded cells (FIG. 1G) revealed the existence of epithelioid phenotype smooth muscle cell features (reviewed by Gittenberger-de Groot A. C, et al PNAS 2000; 97:11307) and markers (αSMA) undetected in the smaller, filtered cells. When further characterized by RT-PCR amplification of RNA, the larger, excluded cells were found to actively express epitheliod markers Calponin and Caldesmon; smooth muscle actin (SMA), and SM-MHC (FIG. 1H, Retained). RT-PCR of RNA from the smaller, endothelial-like cells demonstrated no expression of any of the epitheliod cell markers (FIG. 1H, Filtrated). Note that the intensities of the GAPDH bands are identical for both the cell populations (FIG. 1H), indicating the specific nature of the change in cell phenotype with differentiation.

When the two cell populations arising from the low-density seeding, and culturing of human stem cells (hES) were assessed for cell proliferation capability, the BrdU incorporation assay revealed that the epitheliod, excluded large smooth muscle-like cells are unable to proliferate (FIG. 1I, arrow) while the smaller, endothelial-like progenitor cells clearly incorporate the stain, indicating retention of proliferative ability (FIG. 1I). Taken together, these results indicate that human stem cells, seeded as single cells and not as Embryoid Bodies, and cultured in vitro on a cell-free, two-dimensional matrix, can give rise to proliferating, endothelial-like progenitor cells, which can be separated by filtration from smooth muscle-like precursors.

Example 2

In Vitro Induction of Endothelial, Smooth Muscle and Hematopoietic Cell Differentiation of Human Vasculogenic Progenitor Cells In order to study the differentiation potential of the vasculogenic progenitor cells, cells were recultured on type IV collagen coated dishes, at a lower cell seeding concentration ($2.5\times10^4$ cells/cm$^2$). Smooth muscle cell differentiation was induced by adding platelet-derived growth factor BB (hPDGF-BB), which has been found to induce SMC differentiation in murine (mES), but not human stem cells (Gittenberger-de Groot A. C et al PNAS 2000; 97:11307). After 10–12 days of culture both spindle-like shaped and epithelioid phenotype cells were detected in the culture, along with a concomitant induction of expression smooth muscle cell markers. RT-PCR analysis detected upregulation of specific smooth muscle markers such as smooth muscle α-actin (SMA), smooth muscle myosin heavy chain (SM-MHC), calponin, SM22, and caldesmon (FIG. 2A, v-SMC), notably undetectable in the RNA from non-hPDGF-BB treated cells (FIG. 2A, ESH progenitor cells). Immunofluorescent detection of the human smooth muscle cell marker proteins (αSMA, FIG. 2B; smoothelin, a marker of early smooth muscle development, FIG. 2C; SM-MHC FIG. 2D and Calponin FIG. 2E) confirms the capacity for further in vitro differentiation of human vasculogenic progenitor cells by exposure to hPDGF-BB.

To test the potential of differentiation to endothelial cells, the human vasculogenic progenitor cells were exposed to hVEGF$_{165}$, found to be efficient in murine, but not human endothelial cell induction (Yamashita J, et al. Nature 2000; 408:92). This manipulation resulted in the induction of endothelial cell-specific markers: continuous expression of VE-cad and the appearance of von Willebrand Factor (vWF) stored in Weibel-Palade bodies, as detected by immunofluorescence (FIGS. 2F and 2G, respectively), Dill-Ac-LDL uptake in more mature cells (FIG. 2H) and even stress fibers arrangement in some mature cells (FIG. 2I). Most significantly, growth factor-induced differentiation, with either hPDGF-BB or hVEGF$_{165}$, did not induce a lineage-specific commitment, i.e.: both endothelial and smooth muscle cell types were observed with administration of each of the growth factors. Furthermore, BrdU incorporation into the differentiated cells indicated preservation of proliferative capability in the vascular endothelium growth-factor (VEGF) treated cells (FIG. 2I), and specifically those cells of the smaller morphology, while cells treated with hPDGF-BB exhibited impaired proliferation ability (FIG. 2J). Hematopoietic capability of the isolated progenitor cells was also demonstrated. When the VE-cad-expressing population of filtrated, vasculogenic progenitor cells was cultured in a semisolid medium with cytokines, CFUs indicating hematopoietic colonies (FIGS. 2K–M) were observed. Thus, differentiation of isolated human vasculogenic progenitor cells may be further induced, and controlled, by specific growth factors in vitro, in a cell-free medium, without lineage-specific commitment or loss of proliferative capability.

Example 3

In-vitro Vasculogenesis and Blood Cell Formation by ESH Cells

Crucial events characteristic of vasculogenesis have been induced in vitro using murine embryonic stem cell-derived embryoid bodies (see, for example, Feraud O et al Lab Investig 2001; 81: 1661–89), however efforts to emulate vasculogenic processes in vitro using human pluripotent stem cells have been largely unsuccessful. To study the in-vitro vascularization potential of human vasculogenic progenitor (ESH) cells we used two different 3-dimensional models: type I collagen gel and Matrigel, which have been used to promote 3D vessel-like formation from endothelial cells (Mardi J A and Pratt B M, B.M.J Cell Biol.1988; 106:1375; Kubota Y et al J Cell Biol 1988; 107:1589).

Aggregation of the ESH cells, in the presence of hVEGF and hPDGF-BB supplemented differentiation medium, prior to seeding into type I collagen (FIG. 3A) or on Matrigel (FIG. 3B) clearly induces sprouting and tube-like structures associated with early vasculogenesis and vascularization of both the collagen and Matrigel substrate. Histological sections demonstrate penetration of the endothelial cells into the Matrigel, forming a tube-like network structure characteristic of vascular formation (FIG. 3C). Surprisingly, and of great importance, observation under higher magnification reveals blood cells within these in-vitro cultivated vessels (FIG. 3D, arrow). Electron microscopy further reveals well-formed endothelial-specific Weibel-Palade bodies (WP) in the cell cytoplasm, lipoprotein capsules (Li), endothelial cells forming a lumen (Lu) in the cords and hematopoietic (BC) development within the vessels formed by endothelial cells (EC) within the Matrigel (M) (FIGS. 3E–3G). These results demonstrate, for the first time, isolated human vasculogenic progenitor cells having the capacity to differentiate into functional endothelial cells with lipoprotein metabolism, factor VIII (vWF) production, blood cells, and all components of vascular structures in vitro, under defined conditions.

Example 4

3 Dimensional Scaffold Vascularization

In vitro vascularization of engineered tissues is a critical aspect of regenerative medicine, crucial for the maintenance of cultured tissue viability before and after implantation. Large-diameter vascular structures, suitable for implantation, require a supporting framework, e.g. scaffold, for efficient development and growth. Therefore, the therapeutic potential of human vasculogenic (ESH) progenitor cells was investigated using an in-vitro tissue engineering model, the 3-dimensional alginate scaffold, which has been shown to support in vitro tissue formation from fibroblasts and hepatocytes (Shapiro L, and Cohen S. Biomaterials 1997; 18: 583; and Glicklis R, et al Biotechnol Bioeng 2000; 67:344), but not human vasculogenic progenitors.

When human vasculogenic progenitors were aggregated, as described, and seeded within porous alginate scaffolds, distinct vessel formation around the scaffold pores was observed after 14 days incubation in differentiation medium supplemented with both hVEGF and hPDGF-BB (FIG. 4A, red-staining structures). Higher magnification examination of the vascular wall structure reveals flat, elongated endothelial cells surrounded by smooth muscle cells, typical of vascular morphology (FIG. 4B). Thus, culturing human vasculogenic progenitor (ESH) cells on 3-D scaffolds demonstrated, for the first time, the capability for directed, in-vitro vasculogenesis with differentiated human stem cells, faithful to normal angiogenic development.

Example 5

Human Vasculogenic Progenitor Cell Differentiation as a Model for Angiogenesis

Recent studies have demonstrated that some murine embryonic stem cell (mES) systems are capable of reproducing key events and chronology of the angiogenic process, providing a potentially useful tool with which to investigate mechanisms of angiogenesis (Feraud, 0 et al Lab. Invest. 2001; 81: 1669). Of further significance was the observation that mES cells derived from VE-cad deficient strains of mice (VE-cad –/–) failed to develop endothelial sprouts. However, only embryoid bodies (mEB), and not single cells, were capable of initiation of the vasculogenic events in vitro.

To investigate whether directed, in-vitro vascular development from isolated human vasculogenic progenitor cells accurately reflects physiological processes of angio- and vasculogenesis, the effect of inhibitory antibodies was assessed using BV6, a hVE-cad-specific monoclonal antibody found to inhibit in vitro tube-formation of human endothelial cells (Corada M et al., Blood 2001; 97: 1679).

Suprisingly, the anti-VE-cad monoclonal exhibited a strong inhibitory effect on in vitro vascularization by ESH cells. 7 days after incubation of ESH cells seeded on Matrigel in differentiation medium supplemented with growth factors, the vessels and network structures typical of early vasculogenesis are clearly discernible in the gel (FIG. 5A). Addition of 50 μg/ml of the anti hVE-cad antibody BV6 to the medium clearly disrupted vasculogenesis, inhibiting essential cell sprouting and the formation of tube and network structures (FIG. 5B). Thus, in-vitro, directed differentiation of isolated human vasculogenic progenitor (ESH) cells exhibits sensitivity to known inhibitors of human angiogenesis-vasculogenesis, and as such, provides a model for studying and assessing vascular-related effectors and therapies.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, and patent applications mentioned in this specification are herein incorporated in their entirety by reference into the specification, to the same extent as if each individual publication, patent, or patent application was specifically and individually indicated to be incorporated herein by reference. In addition, citation or identification of any reference in this application shall not be construed as an admission that such reference is available as prior art to the present invention.

What is claimed is:

1. A method of preparing vasculogenic progenitor cells from undifferentiated human or primate embryonic stem (ES) cells, the method comprising:
   (a) culturing individual undifferentiated human or primate ES cells under conditions which prevent cell aggregation and inducing differentiation of the undifferentiated human or primate ES cells into vasculogenic progenitor cells, thereby obtaining a mixed population of cells which comprises the vasculogenic progenitor cells; and
   (b) isolating cells smaller than 50 μm from said mixed population of cells, said cells smaller than 50 μm being vasculogenic progenitor cells.

2. The method of claim 1, wherein said conditions are selected from a group consisting of growth on collagen and cell seeding concentration.

3. The method of claim 1, wherein said isolating is effected via filtration, morphometry and/or densitometry.

* * * * *

```
                              SEQUENCE LISTING

<160> NUMBER OF SEQ ID NOS: 22

<210> SEQ ID NO 1
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 1
ccagctatgt gaagaagaag agg                                                 23

<210> SEQ ID NO 2
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 2
gtgatctcct tctgcattcg gt                                                  22

<210> SEQ ID NO 3
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 3
gagtgtgcag acggaacttc agcc                                                24

<210> SEQ ID NO 4
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 4
gtctgtgccc aacttggggt c                                                   21

<210> SEQ ID NO 5
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 5
ctacaggagc atgctgcagg atcg                                                24

<210> SEQ ID NO 6
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 6
```

```
gcttgcagaa gctgcttctc cagc                                                24
```

<210> SEQ ID NO 7
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 7

```
cgcgaagtgc agtccaaaat cg                                                  22
```

<210> SEQ ID NO 8
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 8

```
gggctggttc ttcttcaatg ggg                                                 23
```

<210> SEQ ID NO 9
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 9

```
aacaacctga aagccaggag g                                                   21
```

<210> SEQ ID NO 10
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 10

```
gctgcttgtt acgtttctgc                                                     20
```

<210> SEQ ID NO 11
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 11

```
agccggcacc tgttgtgcaa                                                     20
```

<210> SEQ ID NO 12
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 12

```
tgacttctcc tgcatgcact                                                     20
```

<210> SEQ ID NO 13
<211> LENGTH: 20
<212> TYPE: DNA
<213> ORGANISM: Artificial sequence

```
<220> FEATURE:
<223> OTHER INFORMATION: Single strand DNA oligonucleotide

<400> SEQUENCE: 13
cagtctgacc agcgtgaaaa                                               20

<210> SEQ ID NO 14
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 14
ggccatccaa atctgtccta                                               20

<210> SEQ ID NO 15
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 15
atcccatttg caaagcttct ggctggc                                       27

<210> SEQ ID NO 16
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 16
tgtgaagcgt ctcacaggtc caggatg                                       27

<210> SEQ ID NO 17
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 17
caacgagaaa atgtcaga                                                 18

<210> SEQ ID NO 18
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 18
ggagccttcc gttctagagt                                               20

<210> SEQ ID NO 19
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 19
atggtgcagc tgagtcctcc                                               20
```

```
<210> SEQ ID NO 20
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 20
tctcattctt gctgagcttc                                              20

<210> SEQ ID NO 21
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 21
agccacatcg ctcagacacc                                              20

<210> SEQ ID NO 22
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 22
gtactcagcg gccagcatcg                                              20
```